(12) United States Patent
Tagawa et al.

(10) Patent No.: US 6,500,398 B1
(45) Date of Patent: Dec. 31, 2002

(54) METHOD AND APPARATUS FOR DECOMPOSING $N_2O$

(75) Inventors: Katsushi Tagawa, Nobeoka (JP); Koji Miura, Nobeoka (JP); Souhei Kodama, Nobeoka (JP); Atsushi Shimizu, Nobeoka (JP); Katsutoshi Tanaka, Nobeoka (JP)

(73) Assignee: Asahi Kasei Kabushiki Kaisha, Osaka (JP)

( * ) Notice: Subject to any disclaimer, the term of this patent is extended or adjusted under 35 U.S.C. 154(b) by 0 days.

(21) Appl. No.: 09/554,705

(22) PCT Filed: Nov. 16, 1998

(86) PCT No.: PCT/JP98/05148
§ 371 (c)(1),
(2), (4) Date: May 18, 2000

(87) PCT Pub. No.: WO99/25461
PCT Pub. Date: May 27, 1999

(30) Foreign Application Priority Data

Nov. 18, 1997 (JP) .............................. 9-316671
Mar. 27, 1998 (JP) ............................ 10-081722

(51) Int. Cl.[7] .............................................. B01D 53/56
(52) U.S. Cl. .................... 423/235.1; 422/171; 422/172; 422/173; 422/177; 423/239.1
(58) Field of Search .................. 423/235, 239.1, 423/580.1; 422/171, 172, 173, 177, 182, 183; 562/543

(56) References Cited

U.S. PATENT DOCUMENTS 3,467,492 A * 9/1969 Newman .................... 423/235
5,167,908 A * 12/1992 Chakraborty ............... 376/301
5,200,162 A * 4/1993 Riley et al. ................. 423/239
5,472,680 A * 12/1995 Reimer et al. .............. 423/405

FOREIGN PATENT DOCUMENTS

| JP | A4914378 | 2/1974 |
| JP | A61257940 | 11/1986 |
| JP | A504027 | 1/1993 |
| JP | A5339003 | 12/1993 |
| JP | A6277453 | 10/1994 |
| JP | A7196639 | 8/1995 |
| JP | A9508346 | 8/1997 |

* cited by examiner

*Primary Examiner*—Stanley S. Silverman
*Assistant Examiner*—Maribel Medina
(74) *Attorney, Agent, or Firm*—Birch Stewart Kolasch & Birch, LLP

(57) ABSTRACT

A low-cost and practically useful method for preventing global warming by decomposing $N_2O$ wherein $N_2O$ contained in an $N_2O$-containing gas to be treated can be decomposed at a relatively low temperature; and an apparatus therefor. That is, a method for preventing global warming comprising, in a process of thermally or catalytically decomposing $N_2O$ in an $N_2O$-containing gas to be treated, dividing the $N_2O$-containing gas stream to be treated in portions, preheating a portion thereof so as to exothermally decompose $N_2O$ in said gas stream to form a hot gas stream, and supplying the remainder of the divided gas stream to be treated into said hot gas stream to thereby continuously decompose $N_2O$, so that global warming is prevented; and an apparatus therefor.

27 Claims, 5 Drawing Sheets

METHOD AND APPARATUS FOR DECOMPOSING $N_2O$

This application is the national phase under 35 U.S.C. §371 of PCT International Application No. PCT/JP98/05148 which has an International filing date of Nov. 16, 1998, which designated the United States of America.

TECHNICAL FIELD

This invention relates to a method for treating a gas causing global warming and an apparatus therefor. More particularly, it relates to a method for preventing global warming by exothermally decomposing nitrous oxide ($N_2O$), which causes global warming, into nitrogen ($N_2$), oxygen ($O_2$) and optionally nitrogen oxides (NO, $NO_2$, etc.) and an apparatus therefor.

BACKGROUND ART

In the process of producing adipic acid, nitric acid is used as an oxidizing agent. It has been an accepted practice to release into the atmosphere nitrous oxide formed as a by-product in the formation of adipic acid from the oxidation of cyclohexanone and/or cyclohexanol with nitric acid.

However, nitrous oxide has recently attracted public attention as one of the gases causing global warming, though it is not as well known as carbon dioxide which is a typical gas causing global warming.

Nitrous oxide evolves mostly from natural soil or farmlands. Thus, the chemical industry causes only a small part of the nitrous oxide evolving on the earth. However, it is considered that the amount of nitrous oxide formed by chemical processes such as the adipic acid production process, which are artificial $N_2O$ sources, can be controlled. Therefore, attempts have been made in recent years to reduce, first of all, nitrous oxide generated from these chemical processes.

There have been proposed various methods for reducing nitrous oxide generated from chemical processes. Many of these proposals relate to methods for decomposing nitrous oxide ($N_2O$) into nitrogen ($N_2$) and oxygen ($O_2$) and optionally nitrogen oxides (NO, $NO_2$). These methods involve two main types for decomposing $N_2O$, namely, thermal decomposition methods wherein decomposition is carried out by heating without using any catalyst and catalytic decomposition methods wherein decomposition is carried out by using a catalyst. Now, each type of these methods will be described.

Known examples of the thermal decomposition methods without using any catalyst include those proposed in, for example, U.S. Pat. No. 2,974,019, JP-A-61-257940, JP-A-5-339003 and JP-W-A-9-508346 (the term "JP-A" as used herein means an "unexamined published Japanese patent application" and the term "JP-W-A" as used herein means an "international patent application published in the Japanese national proceeding"). However, these proposals each suffers from unsolved problems as will be described hereinafter. That is, no satisfactory method for thermally decomposing nitrous oxide has been proposed hitherto.

That is, U.S. Pat. No. 2,974,019 proposes an apparatus by which $N_2O$ is thermally decomposed at a high temperature under elevated pressure (to 1692° C., to 25.5 atm) to give $NO_2$. However, a highly reliable material for this apparatus used to resist the high temperature and elevated pressure is not readily available and makes the apparatus highly expensive. Therefore, this method is used very little in practice.

JP-A-61-257940, which has been applied by the same applicant as in the present invention, discloses that when a discharged gas containing $N_2O$ is preheated and then heated, the thermal decomposition of $N_2O$ starts at about 900° C. and $N_2O$ can be thermally decomposed at 1000° C. or above. In the method of the thermal decomposition of $N_2O$ proposed in this document, it is necessary to control the total content of NO and $NO_2$ to be 10% or less in the $N_2O$-containing gas to be treated. Thus, there arises a problem that an additional step is needed for controlling the discharged gas composition.

JP-A-5-339003 proposes an improved method over the above-mentioned JP-A-61-257940 for thermochemically decomposing $N_2O$ with a flame treatment in the thermal decomposition method. In this method, $N_2O$ is thermochemically decomposed in the presence of flame by the combustion heat of the flame. Therefore, it is feared that the thermochemical reaction in this method should be performed at a considerably higher temperature due to the combustion heat of the flame coupled with the decomposition heat of $N_2O$. In this method wherein the flame is continuously employed in the thermochemical decomposition of $N_2O$, it is unavoidable to use a considerably large amount of fuel for the generation of the flame. As a result, a large amount of a combustion gas is formed and, therefore, the NO and $NO_2$ concentrations in the thermochemically decomposed gas are lowered, which brings about another fear that a large-scaled device (for example, an absorption tower) should be used to recover the NO and $NO_2$.

JP-W-A-9-508346 proposes a method wherein the method of the thermal decomposition of $N_2O$ as disclosed in the above-described JP-A-61-257940 is improved in the preheating portion to thereby produce NO from $N_2O$. That is, this document proposes a method for producing NO from $N_2O$ by heating an $N_2O$-containing gas to about 400 to 700° C. by using a heat exchanger, then heating the gas to about 850° C. without a heat exchanger and using the combustion heat of a combustible gas, etc., thermally decomposing $N_2O$ in the gas at 1000° C. or above, and then quickly cooling the gas thus formed to thereby recover NO. In the case of this method, however, it is needed to heat the whole $N_2O$-containing gas to be treated to 850° C. by using the combustion of a combustible gas, etc. It is therefore unavoidable to use a large amount of the combustible gas. Accordingly, this method suffers from the same problem as in the method proposed by JP-A-5-339003 described above. In this method, furthermore, it is feared that the temperature in the reaction chamber is elevated to a considerably high level, since a large amount of decomposition heat is generated in the reaction chamber from the $N_2O$ holding the combustion heat as described above. Regarding this point, it is described in the specification of this application that the temperature in the reaction chamber might be elevated to 1500° C.

In the thermal decomposition reaction of $N_2O$, the reaction by which $N_2O$ is decomposed into $N_2$ and $O_2$ is an exothermic reaction. Accordingly, there arises a problem that the temperature in the reaction system, where $N_2O$ is thermally decomposed, is remarkably elevated due to the decomposition heat generated in a large amount. As the temperature in the reaction system is elevated, more expensive heat-resistant materials should be employed in the reactor and various devices for treating the gas discharged from the reactor (for example, a heat exchanger, a device for absorbing the thus formed gas, pipes connecting these devices, etc.). In addition, it is also feared that the maintenance of the equipment becomes more difficult thereby. In the conventional proposals as described above, however, no consideration has been given with respect to these problems accompanying the decomposition heat of $N_2O$.

That is to say, no satisfactory method for thermally decomposing nitrous oxide has been proposed hitherto.

As examples of the catalytic decomposition methods with the use of a catalyst, proposals have been made by JPA-5-4027, JP-A-6-277453, etc. However, these proposals each suffer from unsolved problems as will be described hereinafter. That is, no satisfactory method for catalytically decomposing nitrous oxide has been proposed hitherto similar to the case of the thermal decomposition methods.

For example, JP-A-5-4027, which has been applied by the same applicant as in the present invention, proposes a method for catalytically decomposing an $N_2O$-containing discharged gas into $N_2$ and $O_2$ in the presence of a copper(II) oxide catalyst. This document discloses that the reaction temperature preferably ranges from 400 to 600° C.; that it is desirable in case of an adiabatic reaction to supply the gas while diluted with air, etc. into the reactor, since the temperature in the outlet side of the reactor is elevated due to the large reaction heat of the catalytic decomposition; and that the reaction heat of the catalytic decomposition is recovered from the gas as steam after the completion of the catalytic decomposition by using a heat exchanger or the heat is eliminated by diluting the gas with air, etc. after the completion of the catalytic decomposition. However, the treatment of the reaction heat with the use of a heat exchanger or a diluent gas, as proposed by this document, is accompanied by a problem, since the catalytic decomposition heat of $N_2O$ amounts to 19.5 kcal/mol. In case of, for example, catalytically decomposing an $N_2O$-containing gas with an $N_2O$ concentration of 34%, a large amount of decomposition heat is generated so that the temperature is elevated by about 600° C. after the completion of the catalytic decomposition reaction. To eliminate this heat by the method as proposed above, it is necessary to use a large amount of a diluent gas or a large-scaled heat exchanger, which brings about a fear of a greater cost for the heat elimination.

JP-A-6-277453 proposes an improved process for the catalytic decomposition of $N_2O$. It is disclosed in this document that the outflow gas at the outlet of the decomposition zone is cooled and a portion of the thus cooled gas stream is refluxed into the decomposition zone so as to maintain the whole $N_2O$ decomposition zone at a temperature not higher than the maximum allowable temperature Tmax. However, this proposal also suffers from the problem caused by the reaction heat generated in a large amount in association with the decomposition $N_2O$, similar to the case of JP-A-5-4027 as described above.

That is to say, no satisfactory method for catalytically decomposing nitrous oxide has been proposed hitherto.

The invention provides a method for decomposing $N_2O$ by which the unsolved problems encountering in the conventionally proposed methods for decomposing $N_2O$, which have been discussed above in detail, can be solved to thereby prevent global warming through the decomposition of Accordingly, the object of the invention is to provide a practically useful method and an apparatus for preventing global warming by decomposing $N_2O$, by which $N_2O$ contained in an $N_2O$-containing gas to be treated can be efficiently decomposed at a low temperature while efficiently controlling the $N_2O$ decomposition heat thus generated, and NO and $NO_2$ can be recovered, if necessary, and which apply only a small heat load to a device for decomposing $N_2O$ and to other instruments, and need only an extremely small amount of heat energy supplied externally, and require only a low equipment cost and a low driving cost.

DISCLOSURE OF THE INVENTION

The inventors have conducted intensive studies on a method for decomposing $N_2O$, in particular, a method by which the above-described problems in association with the $N_2O$ decomposition heat can be solved. As a result, the inventors have found out a method for exothermally decomposing $N_2O$ which is completely different from the conventional methods for decomposing $N_2O$ as described above and made it possible to solve the above-mentioned object of the invention, thereby completing the invention.

Accordingly, the present invention provides:

1. A method for preventing global warming comprising, a process of thermally or catalytically decomposing $N_2O$ in an $N_2O$-containing gas to be treated, by dividing the $N_2O$-containing gas stream to be treated in portions, preheating a portion thereof so as to exothermally decompose $N_2O$ in said gas stream to form a hot gas stream, and supplying the remainder of the divided gas stream to be treated into said hot gas stream to thereby continuously decompose $N_2O$, so that global warming is prevented.

2. The method for preventing global warming according to the above item 1, wherein said exothermic decomposition of $N_2O$ is performed by thermal decomposition without using any catalyst.

3. The method for preventing global warming according to the above item 2, wherein the remainder of said divided gas to be treated is supplied into plural positions in the flow direction of said hot gas stream.

4. The method for preventing global warming according to the above item 2 or 3, wherein said decomposition of $N_2O$ in the gas to be treated is performed in a state of a substantially plug flow.

5. The method for preventing global warming according to the above item 2 or 3, wherein said preheating is performed by a direct heating system utilizing an oxidative exothermic reaction of a fuel.

6. The method for preventing global warming according to the above item 5, wherein said fuel is hydrogen or methanol.

7. The method for preventing global warming according to the above item 1, wherein said exothermic decomposition of $N_2O$ is performed by catalytic decomposition.

8. The method for preventing global warming according to the above item 7, wherein the remainder of said divided gas to be treated is supplied into plural positions in the flow direction of said hot gas stream and each brought into contact with a catalytic bed respectively.

9. The method for preventing global warming according to the above item 7 or 8, wherein the gas stream, immediately before contacting the catalytic bed, is a mixture with a diluent gas.

10. The method for preventing global warming according to the above item 9, wherein said diluent gas is air and/or the gas, which has been subjected to the catalytic decomposition of $N_2O$ in the gas to be treated.

11. The method for preventing global warming according to the above item 9, wherein the gas having been subjected to the catalytic decomposition of $N_2O$ in the gas to be treated is cooled and then used as the diluent gas.

12. The method for preventing global warming according to the above item 7, 8, 10 or 11, wherein said preheating is performed by mixing the gas to be treated and/or the diluent gas with steam formed by reacting hydrogen and oxygen using a noble metal catalyst.

13. An apparatus for preventing global warming by thermally decomposing $N_2O$ in an $N_2O$-containing gas, comprising:
- (a) an introduction portion for the $N_2O$-containing gas to be treated;
- (b) a preheating portion for the thus introduced gas to be treated;
- (c) a thermal decomposition portion adjacent to the preheating portion, said thermal decomposition portion having means for supplying the gas to be treated, said supplying means being provided at one or more positions in the flow direction of a gas stream; and
- (d) a discharging portion for the thermally decomposed gas.

14. The apparatus for preventing global warming according to the above item 13, wherein said preheating portion is having means of fuel combustion.

15. The apparatus for preventing global warming according to the above item 14, wherein the temperature of the gas stream at the outlet of said discharging portion is controlled to a constant level by controlling the amount of the fuel fed into said fuel-combustion means.

16. The apparatus for preventing global warming according to the above item 13, 14 or 15, wherein said thermal decomposition portion has a porous plate and/or a multi-pipe nozzle in front of and/or at the back of at least one means for supplying the gas to be treated.

17. The apparatus for preventing global warming according to the above item 13, 14 or 15, wherein said porous plate, multi-pipe nozzle and/or inlet of the gas to be treated are located in such a manner that the gas stream flowing towards the means for supplying the gas to be treated flows as a rotary stream.

18. An apparatus for preventing global warming by Bringing $N_2O$ in an $N_2O$-containing gas into contact with a catalytic bed to thereby catalytically decompose $N_2O$, comprising:
- (a) an introduction portion for the gas to be treated and/or a diluent gas;
- (b) a mixing portion for the gas to be treated and/or the diluent gas;
- (c) a mixing portion having one or more means for supplying the gas to be treated and/or the diluent gas at different positions in the longitudinal direction of the apparatus;
- (d) a catalytic decomposition portion having the catalytic bed; and
- (e) a discharging portion for the catalytically decomposed gas.

19. An apparatus for preventing global warming by catalytic decomposition of $N_2O$ in an $N_2O$-containing gas, comprising:
a device which comprises:
- (a) an introduction portion for the gas to be treated and/or a diluent gas;
- (b) a mixing portion for the gas to be treated and/or the diluent gas;
- (c) a catalytic decomposition portion having a catalytic bed; and
- (d) a discharging portion for the catalytically decomposed gas; and
one or more devices each of which comprises:
- (e) an introduction portion for the discharged gas having been catalytically decomposed, the gas to be treated and/or a diluent gas;
- (f) a mixing portion for the discharged gas having been catalytically decomposed, the gas to be treated and/or the diluent gas;
- (g) a catalytic decomposition portion having a catalytic bed; and
- (h) a discharging portion for the catalytically decomposed gas.

20. The apparatus for preventing global warming according to the above item 18 or 19, wherein said mixing portion for the gas to be treated and/or the diluent gas involves a preheating portion for the gas to be treated and/or the diluent gas.

21. A process for producing adipic acid with reduced release of $N_2O$ that causes global warming, comprising:
- (1) a nitric acid-oxidation step in which cyclohexanol land/or cyclohexanone are oxidized with nitric acid to form adipic acid;
- (2) a nitric acid recovery step in which $HNO_3$ is recovered from an $N_2O$-containing gas caused in the nitric acid-oxidation step;
- (3) a $N_2O$ decomposition step in which the remaining $N_2O$-containing gas stream to be treated, from which $HNO_3$ has been recovered, is divided, a portion thereof is preheated to exothermally decompose $N_2O$ in the gas stream to form a hot gas stream, and the remainder of the divided gas stream to be treated is supplied into said hot gas stream to thereby continuously decompose $N_2O$; and
- (4) a $N_2O$ decomposition heat recovery step in which the $N_2O$ decomposition heat emitted from the $N_2O$ decomposition step is recovered.

Figure 1:
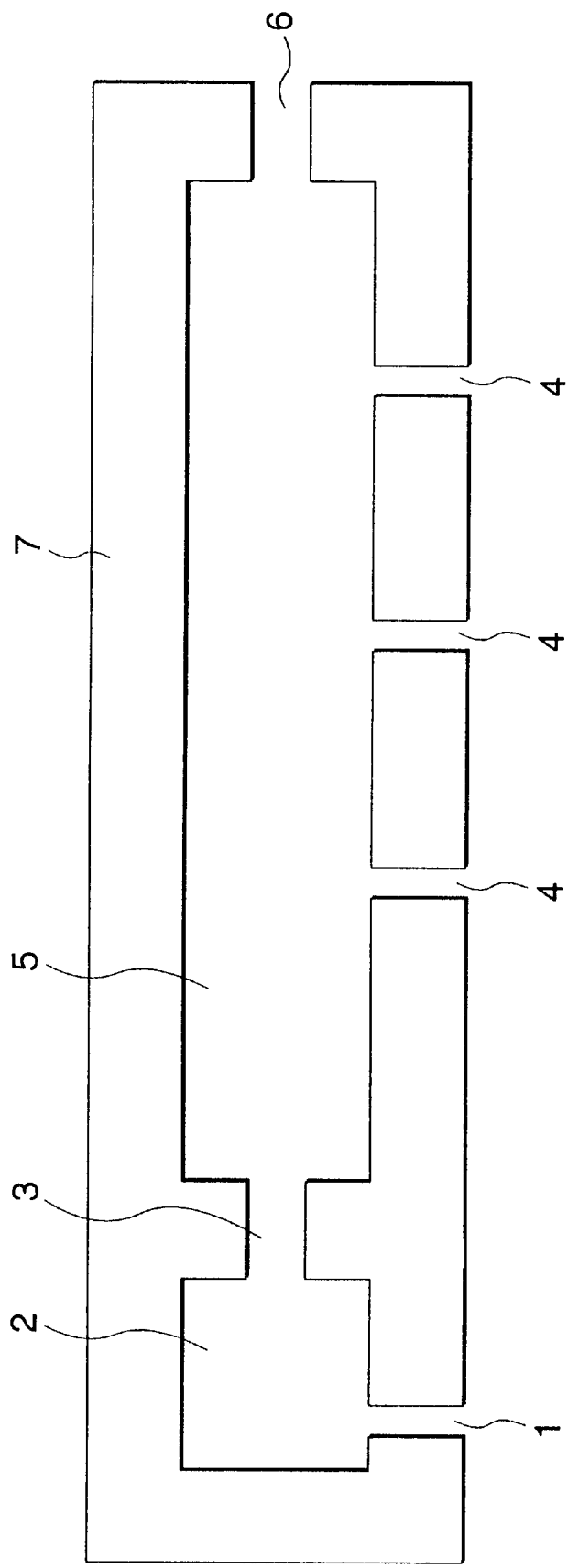
FIG. 1 is a schematic view of an apparatus for thermally decomposing $N_2O$ according to the invention.

In these figures, each numerical symbol has the following meaning:

1: an introduction portion for an $N_2O$-containing gas;
2: a preheating portion;
3: a preheated gas-receiving portion;
4: a supplying portion for the $N_2O$-containing gas;
5: an $N_2O$ thermal decomposition portion;
6: a discharging portion for the thermally decomposed gas;
7: a wall of a thermal decomposition portion;
8: a thermal decomposition portion;
9: a porous plate;
10: a preheating portion;
11: a baffle plate;
12: a supplying portion for the $N_2O$-containing gas;
13: a thermal decomposition portion;
14: a porous plate;

15: a preheating portion;
16: a supplying portion for the N₂O-containing gas;
17: an introduction portion for the gas to be treated;
18: an introduction portion for a diluent gas;
19: a preheating portion;
20: a preheated gas-receiving portion;
21: a space;
22: a catalytic decomposition portion;
23: a mixing portion;
24: a supplying portion for the gas to be treated;
25: a supplying portion for the diluent gas;
26: a discharging portion for the catalytically decomposed gas; and
27: a wall of the catalytic decomposition portion.

BEST MODE FOR CARRYING OUT THE INVENTION

Now, the invention will be described in detail.

The invention aims at preventing global warming by exothermally decomposing $N_2O$ in an $N_2O$-containing gas and thus considerably reducing the release of $N_2O$ gas, which causes global warming, into the atmosphere. With respect to the decomposition of $N_2O$, there have been known reactions represented by the following formulae (1) and (2).

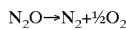  (1)

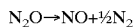  (2).

The reaction of the above formula (1) is an exothermic reaction by which 19.5 kcal/mol of heat is generated, while the reaction represented by the above formula (2) is an endothermic reaction consuming 1.96 kcal/mol of heat. In the case where the heat generated by the reaction of the formula (1) exceeds the heat absorbed in the reaction of the formula (2), then the whole reaction of the decomposition of $N_2O$ is an exothermic decomposition. The term "decomposition of $N_2O$" as used herein means this exothermic decomposition of $N_2O$.

According to the invention, in a process of decomposing $N_2O$ by thermally decomposing or catalytically decomposing $N_2O$ in an $N_2O$-containing gas to be treated, the $N_2O$-containing gas stream to be treated is divided in portions. Then a portion thereof is preheated to thereby exothermally decompose $N_2O$ in the gas stream thereby giving a hot gas stream. Next, the remainder of the divided gas stream to be treated is supplied into the hot gas stream, and thus $N_2O$ is continuously decomposed.

It is preferable in the invention that the $N_2O$-containing gas to be treated is a feedstock gas from the process for producing adipic acid by the nitric acid-oxidation method, though the invention is not restricted thereto. Moreover, it may contain, in addition to $N_2O$, air, nitrogen, oxygen, moisture, carbon dioxide, carbon monoxide, nitrogen monoxide, nitrogen dioxide, hydrocarbons and the like.

The term "thermal decomposition of $N_2O$" as used herein means conversion of $N_2O$ into $N_2$, $O_2$, NO, $NO_2$, etc. by exothermally decomposing $N_2O$ in an $N_2O$-containing gas without using any catalyst. In the invention, the $N_2O$-containing gas stream (i.e., the gas to be treated) is divided into plural gas streams and a portion thereof is preheated.

In this step, it is preferable that the preheating is performed at such a temperature as to substantially allow the initiation of the thermal decomposition of $N_2O$. In the invention, the preferred preheating temperature is from about 750° C. to about 950° C., inclusive. When the preheating temperature is lower than about 750° C., it is feared that $N_2O$ cannot be thermally decomposed at a practical reaction speed when the preheated gas stream is supplied into the $N_2O$ thermal decomposition zone. When the preheating temperature exceeds about 950° C., on the other hand, the substantial thermal decomposition of $N_2O$ starts and thus the advantage of the invention of preheating cannot be achieved. Depending on this preheating temperature, the retention time of the gas to be treated, which is introduced into the thermal decomposition zone close to the preheating zone can be appropriately determined.

A portion of the preheated gas stream to be treated as described above is introduced into the $N_2O$ thermal decomposition zone adjacent to the preheating zone. In this thermal decomposition zone, the self-thermal decomposition of $N_2O$ exothermally starts and thus $N_2O$ is thermally decomposed. Due to the decomposition heat of $N_2O$, the temperature of the gas stream is further elevated in the flow direction of the supplied gas stream, thereby forming a hot gas stream at a high temperature.

In the invention, the remainder of the divided gas stream to be treated is supplied into this hot gas stream. Thus, the temperature of the remainder of the gas to be treated is elevated to the thermal decomposition temperature of $N_2O$ or above and the $N_2O$ contained in the gas to be treated, which has been supplied into the hot gas stream, is continuously thermally decomposed.

It is still preferable to supply the remainder of the divided gas stream to be treated into plural positions (preferably two to five positions) in the flow direction of the above-described hot gas stream. According to the invention, the decomposition heat generated by the self-thermal decomposition of $N_2O$ in the gas stream to be treated, which has been formerly supplied, can be successively and efficiently utilized in elevating the temperature of the gas stream to be treated which is supplied later. It is also possible to control the temperature of the atmosphere in the $N_2O$ thermal decomposition system to an optimum level ranging from a relatively low temperature zone (about 1000° C.) to a moderate temperature zone (about 1300° C.). With an increase in the number of the divided gas streams to be treated, the amount of the fuel to be fed thereinto can be lessened and, in its turn, the energy cost required in maintaining the $N_2O$ decomposition reaction at a definite temperature can be reduced.

In the thermal decomposition of $N_2O$ in the $N_2O$-containing gas according to the invention, it is preferable that the gas stream to be introduced into the $N_2O$ thermal decomposition zone is in a plug flow state. Thus, the decomposition heat generated by the thermal decomposition of $N_2O$ in the gas stream to be treated can be more efficiently utilized in elevating the temperature of the gas stream to be treated supplied into the $N_2O$ thermal decomposition zone later. When the gas stream is in the plug flow state, the temperature of the hot gas stream in the $N_2O$ thermal decomposition zone can be more exactly controlled and, therefore, the remainder of the divided gas stream to be treated can be supplied to desired positions of the hot gas stream in the desired temperature zone.

When the gas stream to be treated is divided and a portion of the thus obtained gas stream is preheated in the invention, the preheating method is not particularly restricted and any well-known method for heating a gas is usable therefor. For example, use may be made of the indirect heating systems such as the pipe heating wherein a pipe which the gas stream to be treated flow through and is externally heated, the gas heat medium heating method wherein the gas stream to be treated is fed into a combustion gas and is heated, the direct heating systems such as the partial combustion heating method wherein a fuel and/or a portion of the gas stream to be treated is subjected to combustion and the gas stream to be treated is heated by the thus generated heat, the heating system with the use of an electric furnace, the microwave heating system, and the like.

Among the preheating methods as cited above, it is particularly preferred in the invention to employ the direct heating system, since the gas stream can be easily and economically heated to a desired temperature thereby, as compared to other heating systems.

Now, the direct heating system will be described more particularly. The partial combustion heating method can be performed by, for example, by reacting $N_2O$ in the gas stream to be treated directly with a fuel and the gas stream to be treated is heated by the reaction heat thus generated. The gas heat medium heating method can be performed by, for example, mixing a hot gas formed by the combustion of a fuel with the gas stream to be treated.

The above-described fuel in the invention means a substance undergoing combustion in the presence of a combustion-supporting gas. Use may be widely made therefor of gas fuels, liquid fuels and solid fuels. Examples of the gas fuels include natural gas, hydrocarbon gas (methane, propane, butane, etc.), hydrogen gas, ammonia and hydrazine. Examples of the liquid fuels include hydrocarbons (gasoline, kerosine, light oil, etc.) and alcohols (methanol, ethanol, etc.). Among gas fuels, it is particularly preferred to use hydrogen gas, since it is superior to other fuels in being free from the generation of carbon dioxide and little affecting the environment. Among the liquid fuels, it is particularly preferred in the invention to use methanol which is inexpensive and easy to handle. Examples of the combustion-supporting gas include air, oxygen and nitrous oxide.

Next, the apparatus of the invention for preventing global warming by thermally decomposing $N_2O$ is now illustrated.

The apparatus of the invention for preventing global warming through the thermal decomposition of $N_2O$, That is, the $N_2O$ thermal decomposition apparatus comprising:

(a) an introduction portion for the $N_2O$-containing gas to be treated;

(b) a preheating portion for the thus introduced gas to be treated;

(c) a thermal decomposition portion adjacent to the preheating portion, said thermal decomposition portion having means for supplying the gas to be treated, said supplying means being provided at one or more positions in the flow direction of a gas stream; and (d) a discharging portion for the thermally decomposed The thermal decomposition portion is a zone wherein $N_2O$ is thermally decomposed.

FIG. 1 is a schematic view illustrating the $N_2O$ thermal decomposition apparatus according to the invention. In FIG. 1, 1 stands for an introduction portion for the $N_2O$-containing gas; 2 stands for a preheating portion for the thus introduced gas; 3 stands for a preheated gas-receiving portion; 4 stands for a supplying portion for the $N_2O$-containing gas; 5 stands for a $N_2O$ thermal decomposition portion wherein the reaction of thermally decomposing $N_2O$ is carried out; 6 stands for a discharging portion for the thermally decomposed gas; and 7 stands for the wall of the thermal decomposition reactor (furnace).

A portion of the gas stream to be treated is supplied from the gas introduction portion 1 to the preheating portion 2 where it is uniformly heated to a temperature at which the thermal decomposition of $N_2O$ can start. When the preheating is performed by the direct heating system as described above, the preheating portion may be provided with a portion of introducing a fuel and a combustion-supporting gas (not shown). In this case, it is favorable that the preheating portion is provided therein with a fuel combustion means such as a combustion burner.

The thus preheated $N_2O$-containing gas is introduced from the preheated gas reception portion 3 into the thermal decomposition portion 5. This thermal decomposition portion 5 is located adjacent to the preheating portion 2 or connected thereto via a preheated gas reception portion 3. In the thermal decomposition portion 5, $N_2O$ is thermally decomposed at the $N_2O$ thermal decomposition temperature or above and a hot gas stream is formed due to the $N_2O$ decomposition heat thus generated.

In the thermal decomposition portion 5, the hot gas stream thus formed is mixed with the remainder of the divided gas stream to be treated, which is supplied from the gas-supplying portion 4. In the case of FIG. 1, three portions 4 are provided for supplying the $N_2O$-containing gas. It is particularly preferable in the invention that there are two to five supplying portions (i.e., the number of stages supplying the gas stream to be treated) in the portion 5 for thermally decomposing the $N_2O$-containing gas.

It is preferable that the portion 4 for supplying the $N_2O$-containing gas is provided with a means for supplying the gas by which the flow condition of the hot gas stream in the thermal decomposition portion 5 can be controlled. For example, one or more of the gas-supplying portions comprising one or more nozzles by which the flow direction and speed of the gas stream to be treated can be controlled. By providing such a means, the gas stream to be treated, the flow direction and speed of which have been appropriately controlled, can be introduced into the thermal decomposition portion and thus flow conditions of the hot gas stream in the thermal decomposition zone can be controlled.

The above-described hot gas stream is combined and mixed with the gas supplied from a first gas-supplying portion 4. Thus, the temperature thereof is temporarily lowered. The temperature of the combined gas stream is elevated as the thermal decomposition of $N_2O$ proceeds and thus a hot gas stream is formed again. This hot gas stream is combined and mixed with the gas stream to be treated supplied from a second gas-supplying portion 4. Thus, $N_2O$ contained in the gas stream to be treated supplied from the gas-supplying portions 4 is thermally decomposed successively. After the completion of the thermal decomposition at a high conversion ratio, the gas is discharged from the thermal decomposition reaction apparatus via the thermally decomposed gas-discharging portion 6.

It is preferable in the invention that the thermal decomposition of $N_2O$ stably proceeds as a chain reaction. To achieve this object, it is preferable that the gas stream in the thermal decomposition portion 5 is substantially in the form of a plug flow. If necessary, the thermal decomposition portion may be provided with a means for controlling the gas stream such as a barrier, a baffle plate, a porous plate, a packing, etc. It is preferable in the invention that the thermal decomposition portion 5 is provided with a porous plate and/or a multi-pipe nozzle (not shown) in front of and/or at the back of the gas-supplying portion 4 so as to make the gas stream into a plug flow.

It is also preferable in the invention that the gas stream is controlled so that the hot gas stream flowing toward the means for supplying the $N_2O$-containing gas flows as a rotary stream. To make the hot gas stream into a rotary stream, the thermal decomposition portion 5 may be provided with a means for controlling the gas stream such as a barrier, a baffle plate, a porous plate, a packing, etc. To control the hot gas stream thereby giving a rotary stream, it is preferable that the gas-supplying portion 4 is provided with a gas-supplying means comprising one or more nozzles by which the flow direction and speed of the gas stream to be treated can be controlled.

In the invention, it is preferable that the temperature of the gas stream at the outlet of the thermal decomposition apparatus (the outlet of the portion 6 for discharging the thermally decomposed gas) is controlled at a definite level. Thus, the instruments can be continuously operated over a long period of time. The outlet temperature varies depending on the temperature of the supplied gas to be treated, the $N_2O$ concentration in the gas stream to be treated, the speed of supplying the gas stream to be treated, the amount of the fuel fed into the preheating portion, etc. To maintain the gas stream at a constant temperature at the outlet of the thermal decomposition apparatus, it is therefore needed to control these factors. In the invention, it is preferable to maintain the gas stream at the outlet of the thermal decomposition apparatus at a constant temperature by regulating the amount of the fuel fed into the preheating portion. Thus, the decomposition temperature can be maintained in a more stable state.

It is preferable in the invention to maintain the supplying temperature of the gas stream to be treated at less than about 750° C. The temperature of the gas flowing but from the thermal decomposition apparatus after the completion of the reaction is not particularly restricted but can be controlled within a wide temperature range from a relatively low temperature region (about 1000° C.) to a moderate temperature region (about 1300° C.). If necessary, use may be made of a temperature of 1500° C. or higher.

The term "catalytic decomposition of $N_2O$" as used herein means that $N_2O$ in an $N_2O$-containing gas is exothermally decomposed with the use of a catalyst (by bringing into contact with a catalyst) into $N_2$ and $O_2$. The invention provides a method for preventing global warming by catalytically decomposing $N_2O$ and an apparatus therefor. Compared with the thermal decomposition method as described above, the catalytic decomposition is performed at a relatively low temperature in this method. Thus, little, if any, NO and $NO_2$ are generated thereby.

As described above, the $N_2O$-containing gas to be treated in the invention may contain, in addition to $N_2O$, air, nitrogen, oxygen, moisture, carbon dioxide, carbon monoxide, nitrogen monoxide, nitrogen dioxide, hydrocarbons and the like. In the case where it is feared that the catalyst might be poisoned by some components contained in the gas to be treated under certain temperature conditions or in the case where it is feared that some unfavorable reaction might occur, it is preferable in the catalytic decomposition method to preliminarily eliminate these components before supplying into the catalytic bed. When the $N_2O$-containing gas also contains nitrogen monoxide and nitrogen dioxide poisoning a palladium catalyst, etc., for example, it is preferable that these components are preliminarily oxidized and absorbed in an absorption column and the mist moisture is eliminated before using as the gas to be treated in the invention. Therefore, the gas to be treated in the invention may be a gas from which other components have been eliminated before supplying into the $N_2O$ decomposition apparatus or a gas which has been mixed with other gases, etc.

The present invention is not restricted by the kind of the catalyst for decomposing $N_2O$. To achieve the objects of the invention, however, it is preferable to use those containing copper, nickel, iron, cobalt, palladium, or oxides or complex oxides of these metals. It is preferable that the catalyst is carried on a carrier. As the carrier, those having appropriate pores and showing a high heat stability may be selected. Preferred examples of the catalyst carrier to be used in the invention include oxides and complex oxides of aluminum, silicon, titanium, magnesium and zirconium. As aluminum oxides among these carriers, it is still preferable to use α-alumina, β-alumina or γ-alumina. As the silica/alumina complex oxides, it is still preferable to use zeolite such as ZSM5. As the titanium oxides, it is still preferable to use those of the anatase and rutile types. It is also preferable to use zirconia which has a high heat resistance. Furthermore, it is preferable to use a carrier obtained by mixing these carriers as cited above. In the invention, the catalyst may be carried on the carrier by a well-known method. For example, the carrier is impregnated with an aqueous solution of a water-soluble salt of a metal catalyst and then baked.

A catalytic system which is particularly preferred in the invention is one having an $N_2O$ catalytic decomposition temperature of from 200 to 800° C., still more preferably from 300 to 700° C.

In a catalytic system having a catalytic decomposition temperature higher than the temperature as specified above, the decomposition heat generated in association with the catalytic decomposition of $N_2O$ can be more efficiently utilized in the subsequent $N_2O$ catalytic decomposition by applying the method of catalytically decomposing $N_2O$ according to the invention.

In the invention, the gas to be treated is divided into gas streams. Then, a portion of the divided gas streams (i.e., one of plural gas streams) is preheated and introduced into an $N_2O$ catalytic decomposition zone wherein $N_2O$ in the gas to be treated is catalytically decomposed to form a hot gas stream. Next, the remainder of the divided gas to be treated is supplied into this hot gas stream. Thus, the temperature of the remainder of the gas streams to be treated can be elevated to a temperature higher than the temperature at which the catalytic decomposition reaction of $N_2O$ starts. Then the gas stream is passed through a catalytic bed so as to catalytically decompose $N_2O$ in the gas to be treated continuously. The catalytic bed serves as the catalytic decomposition zone of $N_2O$.

It is preferable that the remainder of the divided gas to be treated is supplied to plural positions in the flow direction of the above-described hot gas stream. The thus supplied gas to be treated is mixed with the above-described hot gas stream at each of the plural positions as described above and then brought into contact with the catalytic bed located at the back of each supplying position. According to the invention, therefore, $N_2O$ in the gas to be treated, which has been formerly supplied, is catalytically decomposed and the decomposition heat thus generated can be efficiently and successively utilized in elevating the temperature of the gas stream to be treated, which is supplied thereafter. It is particularly preferred that two to four positions for supplying the divided gas stream to be treated as described above are formed. With an increase in the number of the divided gas streams to be treated, the amount of the diluent gas to be employed can be lessened and, in its turn, the energy cost required in maintaining the $N_2O$ decomposition reaction at a definite temperature can be reduced.

In the invention, the gas stream to be treated is divided and introduced into the catalytic decomposition apparatus via plural inlets as described above. In this step, the division ratio of the gas to be treated may be appropriately determined by taking into consideration the $N_2O$ concentration in the gas to be treated, the $N_2O$ decomposition temperature of the catalyst system employed and the treating capability of the catalytic bed employed. To improve the effect achieved by supplying the gas to be treated in portions, it is still preferable that, when Q $Nm^3/H$ of the gas to be treated is introduced into the anterior catalytic bed, then the amount of the gas to be introduced into the Posterior catalytic bed adjacent thereto is controlled to 1.1 to 3.0Q $Nm^3/H$, still preferably 1.2 to 2.7Q $Nm^3/H$. With respect to the catalytic bed volume, similarly, when catalytic beds have the same catalytic system and the same inlet and outlet temperatures and the volume of the anterior catalytic bed is V $m^3$, then it is preferable that the volume of the posterior catalytic bed is controlled to 1.1 to 3.0 V $m^3$, still preferably form 1.2 to 2.7 V $m^3$.

As described above, the gas to be treated is divided and a portion thereof is preheated in the invention. The preheating method is not particularly restricted in the catalytic decomposition method too but any well-known method for heating a gas is usable therefor. For example, use may be made of the indirect heating systems such as the pipe heating wherein a pipe through which the gas stream to be treated flow is externally heated, the gas heat medium heating method wherein the gas stream to be treated is fed into a combustion gas and heated, the direct heating systems such as the partial combustion heating method wherein a fuel and/or a portion of the gas stream to be treated is subjected to combustion and the gas stream to be treated is heated by the thus generated heat, the heating system with the use of an electric furnace, the microwave heating system, and the like. It is also possible to use a preheating method wherein a combustible gas (for example, hydrogen gas) is reacted with an oxidative gas (for example, oxygen gas) by using a catalyst and the obtained reaction mixture is mixed with the gas to be treated. Among the preheating methods as cited above, it is particularly preferred in the invention to employ the method wherein hydrogen gas is reacted with oxygen in the air with the use of a noble metal catalyst and then the steam thus generated is used as a preheat source, since preheating can be started from a low temperature and the preheating temperature can be controlled over a broad scope in this method.

In the method of catalytically decomposing $N_2O$ according to the invention, a diluent gas can be used if needed. This diluent gas may be used in the catalytic decomposition system without being restricted to any definite position. It may be used in the case where the temperature of the gas stream is to be controlled at a definite level. That is to say, when the gas to be treated contains $N_2O$ only at a low concentration and thus there is no fear of an unnecessary increase in the temperature due to the generation of the decomposition heat, for example, then no diluent gas is needed. When $N_2O$ is contained at a high concentration, on the contrary, or the catalytic system employed is available within only a specific narrow reaction temperature range, then it is preferable to use a diluent gas so as to prevent an increase in the temperature of the gas stream after the decomposition or to control the temperature of the gas stream within the specific range.

When a diluent gas is employed in the invention, it is preferable that the diluent gas is supplied from the same position from which the gas to be treated is supplied. The diluent gas may be selected from those which are free from catalyst-poisoning substances or $N_2O$ decomposition reaction inhibitors. Particularly preferred examples of the diluent gas to be used in the invention include air and/or the $N_2O$-containing gas after the catalytic decomposition of $N_2O$, since these gases are inexpensive, readily available and easy to handle.

The catalytic decomposition of $N_2O$, which is the subject of the invention, is an irreversible reaction by which nitrogen and oxygen are generated and thus the gas volume is increased. It is therefore considered advantageous to elevate the operation pressure of the catalytic bed so as to increase the amount of the gas to be treated and reduce the scale of the equipment. However, it is said that pure $N_2O$ gas would undergo an explosive reaction under elevated pressure. Therefore, the inventors consider that $N_2O$ might undergo an explosive reaction under an excessively elevated pressure even in a mixed gas system. Accordingly, it is preferable in the invention to control the operation pressure of the catalytic bed to from atmospheric pressure to 0.5 MPa, still more preferably from atmospheric pressure to 0.3 MPa. The same applies to the pressure in the thermal decomposition method as described above.

Either the thermal decomposition method or the catalytic decomposition method according to the invention is more appropriately applicable to an $N_2O$-containing gas having an $N_2O$ concentration of 60% by volume or less. It is still more preferable that the $N_2O$ concentration in the gas to be treated ranges from 2 to 50% by volume. When the $N_2O$ concentration in the gas to be treated exceeds 60% by volume, there arises a fear of the explosive decomposition behavior sown by pure $N_2O$ gas.

In the invention, the $N_2O$ concentration of the gas stream at the inlet of each catalytic bed may be appropriately determined so as to successfully achieve the objects of the invention. The $N_2O$ concentration preferably ranges from 2 to 20% by volume, still more preferably from 5 to 15% by volume. When the $N_2O$ concentration of the gas at the inlet of the catalytic bed is less than 2% by volume, the heat generated by the catalytic decomposition can result in only a small increase in the temperature at the outlet of the catalytic bed. In this case, it is feared that the obtained gas stream cannot be efficiently and successively utilized in elevating the temperature of the gas stream to be treated, which is supplied thereafter. When the $N_2O$ concentration of the gas at the inlet of each catalytic bed exceeds 20% by volume, on the other hand, the temperature at the outlet of the catalytic bed is excessively elevated due to the heat generated by the catalytic decomposition. In this case, the thermal deterioration of the catalyst is accelerated and, furthermore, there arise a fear that the equipment will become damaged.

Next, the apparatus of the invention for preventing global warming by catalytically decomposing $N_2O$, that is, an $N_2O$ catalytic decomposition apparatus will become illustrated.

The $N_2O$ catalytic decomposition apparatus of the invention is an apparatus wherein an $N_2O$-containing gas to be treated is brought into contact with a catalytic bed to thereby catalytically decompose $N_2O$. This apparatus comprising:

(a) a introduction portion for the gas to be treated and/or a diluent gas;

(b) a mixing portion for the gas to be treated and/or the diluent gas;

(c) a mixing portion having one or more means for supplying the gas Lo be treated and/or the diluent gas at different positions in the longitudinal direction of the apparatus;

(d) a catalytic decomposition portion having the catalytic bed; and (e) a discharging portion for the catalytically decomposed gas.

In another embodiment, the $N_2O$ catalytic decomposition apparatus of the invention is an apparatus by which $N_2O$ in an $N_2O$-containing gas is catalytically decomposed. This apparatus comprises:

a device which comprises:
- (a) a introduction portion for the gas to be treated and/or a diluent gas;
- (b) a mixing portion for the gas to be treated and/or the diluent gas;
- (c) a catalytic decomposition portion having a catalytic bed; and
- (d) a discharging portion for the catalytically decomposed gas; and one or more devices each of which comprises:
- (e) a introduction portion for the discharged gas having been catalytically decomposed, the gas to be treated and/or a diluent gas;
- (f) a mixing portion for the discharged gas having been catalytically decomposed, the gas to be treated and/ or the diluent gas;
- (g) a catalytic decomposition portion having a catalytic bed; and
- (h) a discharging portion for the catalytically decomposed gas.

In each case, the catalytic bed serves as the above-mentioned $N_2O$ decomposition zone.

In the invention, it is an effective means for regulating the $N_2O$ decomposition reaction, to preheat the gas to be treated and/or the diluent gas. Therefore, it is preferable that the mixing portion for the gas to be treated and/or the diluent gas is also provided with a part in which the gas to be treated and/or the diluent gas are preheated.

Figure 4:
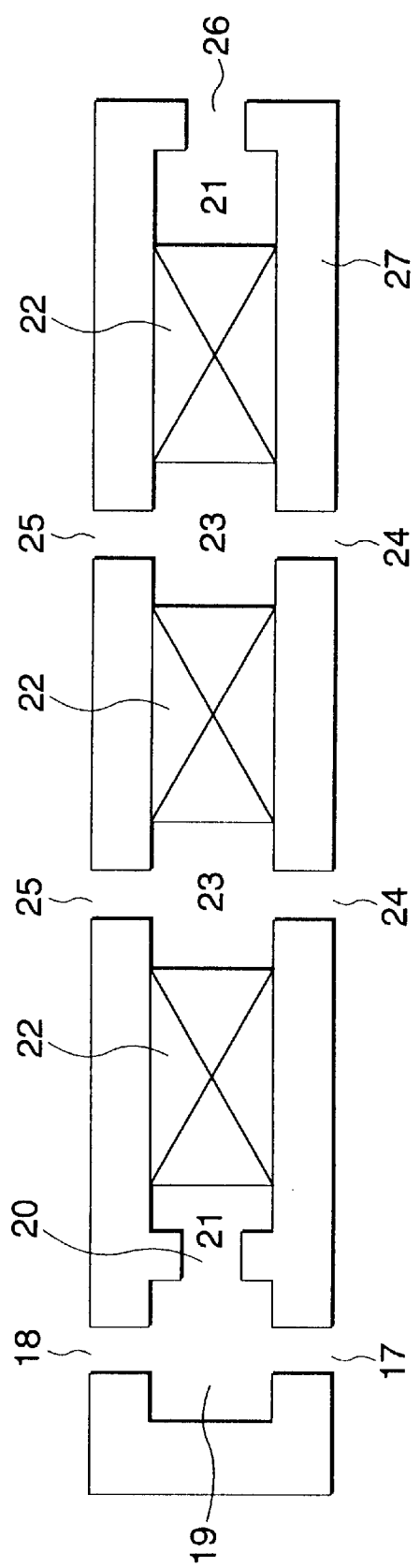
FIG. 4 is a model view of an apparatus for catalytically decomposing $N_2O$ provided with plural catalytic beds according to the invention.
Figure 5:
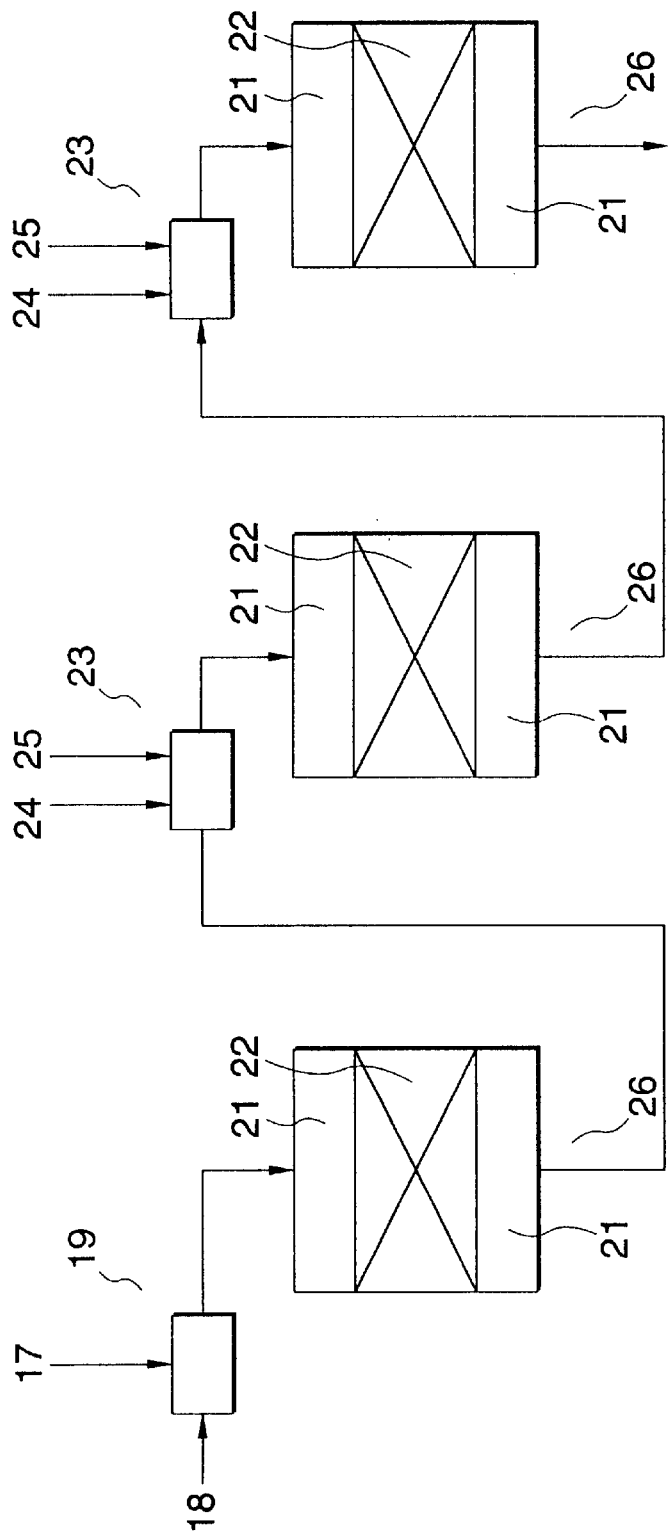
FIG. 5 is a model view of an apparatus for catalytically decomposing $N_2O$ provided with plural catalytic beds independent from each other according to the invention.

FIGS. 4 and 5 are schematic views illustrating the $N_2O$ catalytic decomposition apparatus of the invention.

As FIG. 4 shows, the catalytic decomposition apparatus according to the invention may have plural catalytic beds in a single decomposition apparatus. Alternatively, the decomposition apparatus may comprise independent catalytic beds connected to each other, as FIG. 5 shows.

In FIGS. 4 and 5, 17 stands for an introduction portion for the gas to be treated; 18 stands for an introduction portion for a diluent gas; 19 stands for a preheating portion for the introduced gas; 20 stands for a preheated gas-receiving portion; 21 stands for a space; 22 stands for a catalytic decomposition portion; 23 stands for a mixing portion; 24 stands for a supplying portion for the gas to be treated; 25 stands for a supplying portion for the diluent gas; 26 stands for a discharging portion for the catalytically decomposed gas; and 27 stand for the wall of the catalytic decomposition reactor.

In FIG. 4, a portion of the gas to be treated and the diluent gas are introduced, via the gas introducing portions 17 and 18, into the preheating portion 19 where these gases are uniformly preheated to the initiation temperature of the $N_2O$ catalytic decomposition reaction with the use of the catalyst. The $N_2O$-containing gas thus preheated is transported to the preheated gas receiving portion 20 and then to the catalytic decomposition portion 22. The catalytic decomposition portion 22 is located adjacent to the preheating portion 19 or connected thereto via the preheated gas-receiving portion 20. In this catalytic decomposition portion 22, $N_2O$ is catalytically decomposed and a hot gas stream is formed by the $N_2O$ decomposition heat thus generated. In the mixing portion 23, the hot gas stream formed above is mixed with the remainder of the divided gas to be treated, which is supplied from the supplying portion for the gas to be treated, and the diluent gas, which is supplied from the supplying portion for the diluent gas, to thereby attain a definite concentration and a definite Temperature. Subsequently, $N_2O$ is catalytically decomposed in the catalytic decomposition portion 22. In the case as shown in FIG. 4, two supplying portions 24 for the gas to be treated are provided. In the invention, it is particularly preferred that the catalytic decomposition portion 22 is provided with two to four portions of supplying the $N_2O$-containing gas. In the case shown in FIG. 4, similarly, two portions 25 of supplying the diluent gas are provided. In the invention, it is particularly preferred to provide two to four portions of supplying the diluent gas.

Subsequently, $N_2O$ contained in the gas to be treated, which has been supplied from the supplying portion 24 for the gas to be treated, is successively decomposed with the catalyst. Finally, the catalytically decomposed gas is discharged from the catalytic decomposition apparatus via the portion 26 for discharging the catalytically decomposed gas.

Although the above description has been made by reference to FIG. 4, the same applies substantially to the To stably perform the catalytic decomposition reaction of $N_2O$ with the use of the catalyst, it is preferable in the invention that the apparatus is provided with a porous plate and/or a contraction portion (not shown) in front of and/or at the back of the mixing portion 23 so as to give a uniform gas stream after mixing. It is also possible to insert a structure capable of mixing gases (a baffle plate, a packing, etc.) into the mixing portion 23. To make the hot gas stream in the reactor a rotary stream, it is preferable that the portion 24 of supplying the $N_2O$-containing gas and the portion 25 of supplying the diluent gas are provided each a means of supplying gas comprising one or more nozzles by which the flow direction and speed of the supplied gas can be controlled.

The methods for controlling the gas flow and gas temperature to be used in the invention are not particularly restricted. However, it is favorable that the gas to be treated is supplied to each catalytic bed in an amount determined depending on the amount of the catalyst packed into the corresponding bed so that the gas streams have substantially the same $N_2O$ concentration and the same gas temperature at the inlet of the respective catalytic bed. Thus, the inlet and outlet temperatures of each catalytic bed can be controlled to the desired level.

In the invention, the gas to be treated is divided and a portion thereof is supplied into a first catalytic decomposition portion. Thus, the subsequent catalytic decomposition and thereafter (i.e., the catalytic decomposition at the second stage and thereafter) can be performed by heating the gas to be treated up to the reaction initiation temperature, either totally or partly, with the use of the heat obtained by mixing the gas to be treated with the hot gas supplied from the prior catalytic decomposition portion. Accordingly, the size of a heat exchanger of the gas to be treated required in the reaction system can be reduced. According to the invention, the diluent gas may be supplied, preferably in the form of a gas mixture with the gas to be treated, into each of the catalytic decomposition portions to thereby control the temperature over the whole catalytic decomposition zone. Thus, the temperature of each catalytic bed can be easily controlled and the total amount of the diluent gas can be reduced. As a result, a smaller device for feeding the diluent gas can be used and thus the operation cost and the investment in equipment can be remarkably reduced.

From the viewpoint of efficiently utilizing the heat maintained by the decomposed gas stream, it is preferable in the invention that the gas flowing out from the $N_2O$ decomposition apparatus after the completion of the reaction is introduced into a boiler having a common structure and the reaction heat is recovered as steam. It is also preferable that the gas to be treated is subjected to heat-exchange with the gas after the completion of the reaction, which has been cooled by the boiler, thereby heating the gas to be treated, which is supplied into the reaction apparatus of the invention.

It is also preferable that nitrogen oxides (NO, $NO_2$) contained in the gas flowing out from the reactor after the completion of the thermal decomposition are brought into contact with water and air to thereby recover NO and $NO_2$ as an aqueous nitric acid solution. As described above, it is preferable that the gas to be treated in the invention (i.e., the $N_2O$-containing gas) is a feedstock gas from the process of producing adipic acid by the nitric acid-oxidation method. When nitrous oxide discharged from an adipic acid plant is to be thermally decomposed by the method of the invention, it is preferable that the recovered aqueous nitric acid solution as described above is reused in the production of adipic acid. When it is unnecessary to reuse the NO and $NO_2$ thus formed, it is preferable that NO and $NO_2$ contained in the discharged gas flowing out from the above-described boiler or heat exchanger are reduced in the presence of a catalyst. The reduction may be carried out by, for example, reacting the discharged gas containing NO and $NO_2$ with $NH_3$ in the presence of a catalyst to thereby convert NO and $NO_2$ into $N_2$ and $H_2O$. Thus, the gases formed after the completion of the thermal decomposition can be made causing no pollution.

As the above description clearly indicates, the method for preventing global warming and the apparatus therefor according to the invention are preferably applicable to an $N_2O$-containing gas, in particular, an $N_2O$-containing gas generated from a chemical plant with the use of nitric acid as an oxidizing agent and an $N_2O$-containing feedstock gas. The method and apparatus of the invention are preferably usable, in particular, in the process for producing adipic acid.

Accordingly, the invention is particularly preferred to be applicable to a process for producing adipic acid with extremely reduced release of $N_2O$ causing global warming, which process involves:

(1) a nitric acid-oxidation step in which cyclohexanol and/or cyclohexanone are oxidized with nitric acid to form adipic acid;

(2) a nitric acid recovery step in which $HNO_3$ is recovered from an $N_2O$-containing gas caused in the nitric acid-oxidation step;

(3) an $N_2O$ decomposition step in which the remaining $N_2O$-containing gas stream to be treated, from which $HNO_3$ has been recovered, is divided, a portion thereof is preheated to exothermally decompose $N_2O$ in the gas stream to form a hot gas stream, and the remainder of the divided gas stream to be treated is supplied into said hot gas stream to thereby continuously decompose $N_2O$; and (4) an $N_2O$ decomposition heat recovery step in which the $N_2O$ decomposition heat emitted from the $N_2O$ decomposition step is recovered.

EXAMPLES

The present invention will be described in greater detail by reference to the following Examples, but the invention should not be construed as being limited thereto.

Example 1

$N_2O$ in an $N_2O$-containing gas (a feedstock gas) to be treated, which had been discharged from an adipic acid plant and had the composition and flow rate as given in Table 1 was thermally decomposed.

Figure 2:
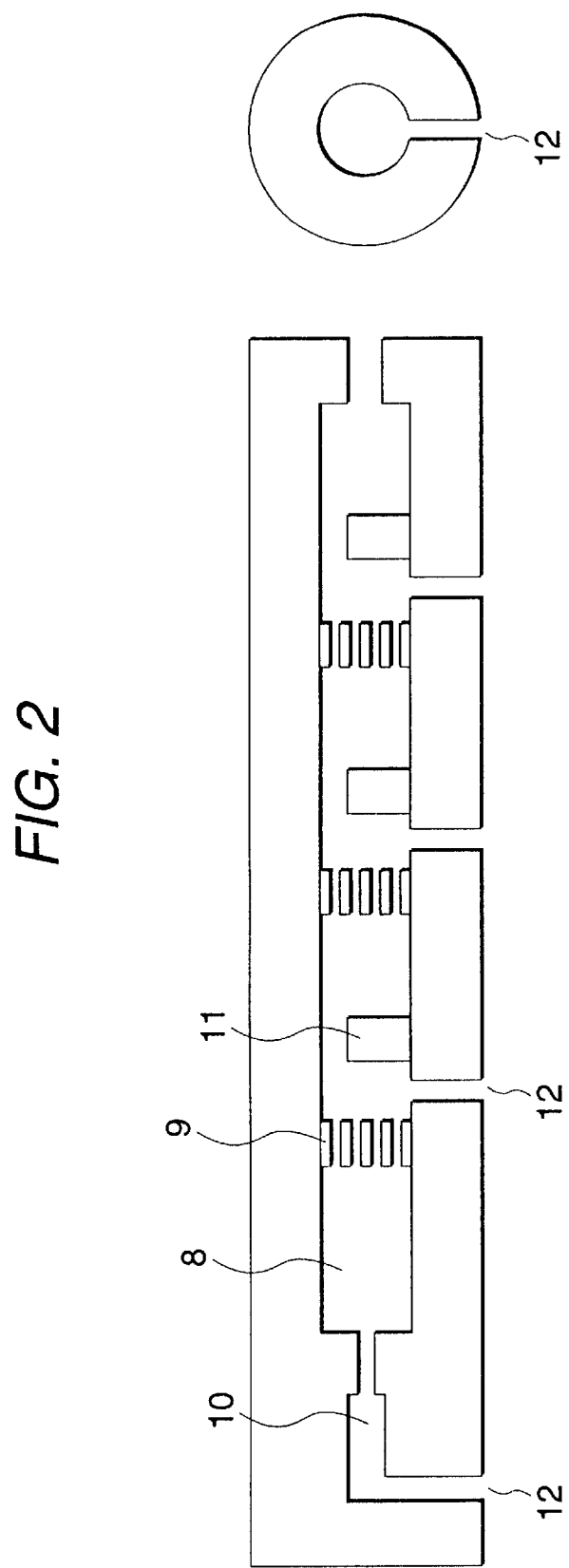
FIG. 2 is a schematic view of a thermal decomposition apparatus used in Example 1.

FIG. 2 is a schematic view of the thermal decomposition apparatus.

A thermal decomposition reaction furnace (thermal decomposition portion 8) employed was one made of heat resistant bricks and having a cylindrical shape with 450 mm in inner diameter and 4750 mm in length. The wall thickness thereof was 300 mm. The inside of the furnace was divided in series into four thermal decomposition chambers ($N_2O$ decomposition zones), having a space of almost the same volume, with porous plates made of heat resistant bricks (thickness: 200 mm). That is, the number of the supplying stage of the gas to be treated was four. The gas to be treated, which had been divided and preheated was fed into the first reaction chamber, while the remainder of the divided gas to be treated was introduced into the second, third and fourth reaction chambers. The second, third and fourth reaction chambers were each provided with an inlet of the gas to be treated immediately after the hot gas stream was fed thereinto. Further, the second, third and fourth chambers are provided each with a baffle plate made of heat resistant bricks (thickness: 200 mm, height: 300 mm) at the back of the above-described inlet of the gas to be treated at a distance of 150 mm from the porous plate from which the hot gas stream was fed. A preheating portion, which was made of heat resistant bricks similar to the thermal decomposition portion, had a cylindrical shape with a space of 200 mm in inner diameter and 500 mm in length. It was provided with an inlet of the gas to be treated at one end while the other end was connected to the thermal decomposition portion. Into this preheating portion, hydrogen corresponding to 12 kcal per 1 $Nm^3$ of the gas to be treated was introduced with air at a rate of 1.3 $Nm^3$/hr. Then it was subjected to combustion in the preheating portion and uniformly mixed with the gas to be treated introduced into the preheating portion at 17.9 $Nm^3$/hr. The temperature of the gas to be treated was adjusted to 550° C. The temperature of the gas stream introduced from the preheating portion to the first reaction chamber was 830° C. The gas to be treated at 550° C. was supplied into the second, third and fourth reaction chambers respectively at flow rates of 34.1 $Nm^3$/hr, 72.6 $Nm^3$/hr and 155.4 $Nm^3$/hr. The mixtures of the hot gas stream with the gas to be treated at the inlets of the second, third and fourth reaction chambers had each a temperature of 830° C. The pressure within the furnace was 1.25 $kg/cm^2$ (gauge pressure).

The temperature of the gas stream discharged from the thermal decomposition reaction furnace was 1163° C. and $N_2O$ contained in the supplied gas to be treated had been thus thermally decomposed at a ratio of 99% or more.

Example 2

$N_2O$ contained in a gas to be treated discharged from an adipic acid plant was thermally decomposed as in Example 1 but the temperature of the supplied gas to be treated being 300° C.; the flow rate of hydrogen supplied into the preheating portion being 7.2 $Nm^3$/hr; and the flow rates of the gas to be treated supplied into the preheating portion and the second, third and fourth reaction chambers being respectively 55.7 $Nm^3$/hr, 60.0 $Nm^3$/hr, 72.9 $Nm^3$/hr and 91.4 $Nm^3$/hr.

The pressure within the furnace was 1.25 $kg/cm^2$. The gas stream mixtures in the preheating portion and at the inlets of the second, third and fourth reaction chambers had each a temperature of 830° C. The temperature of the gas stream discharged from the thermal decomposition reaction furnace was 1027° C. and N$_2$O contained in the supplied gas to be treated had been thus thermally decomposed at a ratio of 99% or more.

Example 3

N$_2$O contained in a gas to be treated was thermally decomposed as in Example 1 but the temperature of the supplied gas to be treated being 700° C.; the flow rate of hydrogen supplied into the preheating portion being 0.1 Nm$^3$/hr; and the flow rates of the gas to be treated supplied into the preheating portion and the second, third and fourth reaction chambers being respectively 3 Nm$^3$/hr, 12.0 Nm$^3$/hr, 50.6 Nm$^3$/hr and 214.4 Nm$^3$/hr.

The pressure within the furnace was 1.25 kg/cm$^2$. The gas stream mixtures in the preheating portion and at the inlets of the second, third and fourth reaction chambers had each a temperature of 830° C. The temperature of the gas stream discharged from the thermal decomposition reaction furnace was 1263° C. and N$_2$O contained in the supplied gas to be treated had been thus thermally decomposed at a ratio of 99%.

Example 4

N$_2$O contained in a gas to be treated was thermally decomposed as in Example 1 but the flow rate of hydrogen supplied into the preheating portion being 1.2 Nm$^3$/hr; and the flow rates of the gas to be treated supplied into the preheating portion and the second, third and fourth reaction chambers being respectively 19.7 Nm$^3$/hr, 36.1 Nm$^3$/hr, 73.4 Nm$^3$/hr and 150.8 Nm$^3$/hr.

The pressure within the furnace was 1.25 kg/cm$^2$. The gas stream mixtures in the preheating portion and at the inlets of the second, third and fourth reaction chambers had each a temperature of 800° C. The temperature of the gas stream discharged from the thermal decomposition reaction furnace was 1131° C. and N$_2$O contained in the supplied gas to be treated had been thus thermally decomposed at a ratio of 99% or more.

Example 5

The inside of the thermal decomposition reaction furnace as in Example 1 was divided in series into first, second and third chambers, having a space of almost the same volume, with porous plates made of heat resistant bricks (thickness: 200 mm). The inlets of the gas to be treated and the baffle plates were arranged as in Example 1. The preheating portion had the same volume as in Example 1.

N$_2$O contained in a gas to be treated was thermally decomposed as in Example 1 but the flow rate of hydrogen supplied into the preheating portion being 2.9 Nm$^3$/hr; and the flow rates of the gas to be treated supplied into the preheating portion and the second and third reaction chambers being respectively 40.4 Nm$^3$/hr, 76.5 Nm$^3$/hr and 163.1 Nm$^3$/hr.

The pressure within the furnace was 1.25 kg/cm$^2$. The gas stream mixture in the preheating portion a at the inlets of the second and third reaction chambers had each a temperature of 830° C.

Example 6

The inside of the thermal decomposition reaction furnace as in Example 1 was divided in series into first and second chambers, having a space of almost the same volume, with a porous plate made of heat resistant bricks (thickness: 200 mm). The inlets of the gas to be treated and the baffle plates were arranged as in Example 1. The preheating portion had the same volume as in Example 1. N$_2$O contained in a gas to be treated was thermally decomposed as in Example 1 but the flow rate of hydrogen supplied into the preheating portion being 6.9 Nm$^3$/hr; and the flow rates of the gas to be treated supplied into the preheating portion and the second reaction chamber being respectively 96.6 Nm$^3$/hr and 183.4 Nm$^3$/hr.

The pressure within the furnace was 1.25 kg/cm$^2$. The gas stream mixtures in the preheating portion and at the inlet of the second reaction chamber had each a temperature of 830° C. The temperature of the gas stream discharged from the thermal decomposition reaction furnace was 1200° C. and N$_2$O contained in the supplied gas to be treated had been thus thermally decomposed at a ratio of 99% or more.

Example 7

N$_2$O in an N$_2$O-containing gas to be treated, which had been discharged from an adipic acid plant and had the composition and flow rate as given in Table 1 was thermally decomposed.

Figure 3:
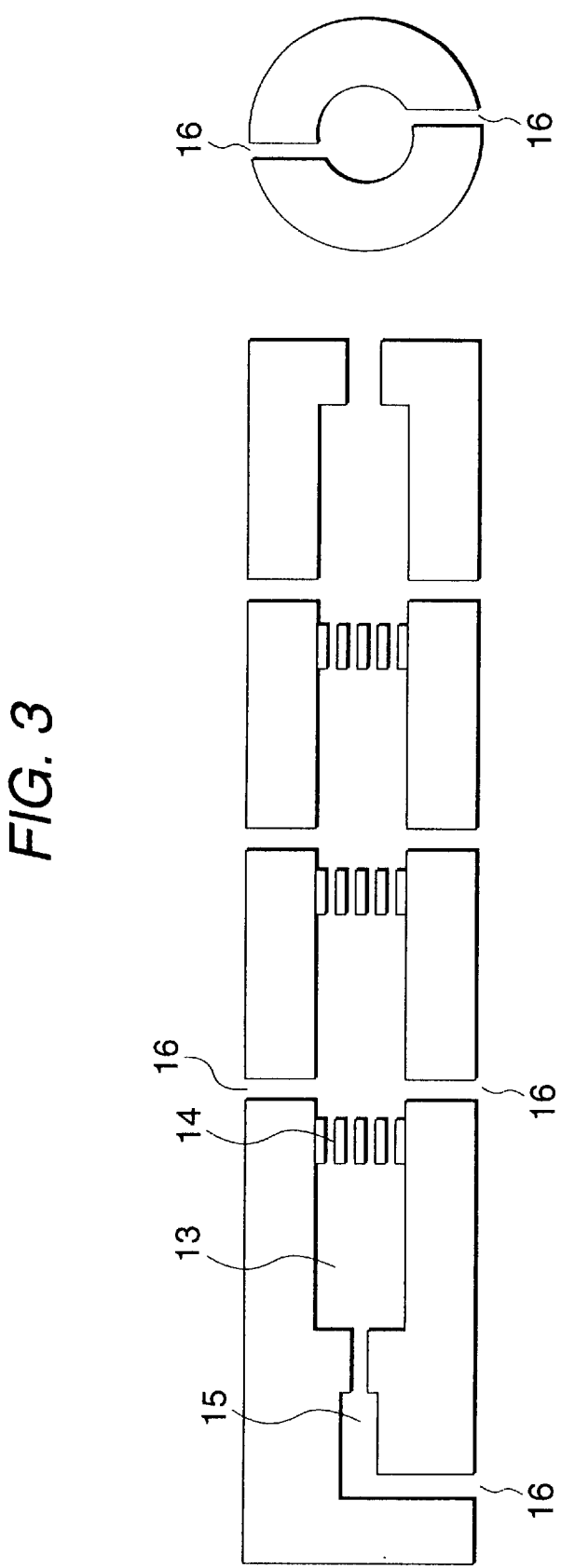
FIG. 3 is a schematic view of a thermal decomposition apparatus used in Example 7.

FIG. 3 is a schematic view of the thermal decomposition apparatus.

A thermal decomposition reaction furnace (thermal decomposition portion) employed was one made of heat resistant bricks and having a cylindrical shape with 400 mm in inner diameter and 4300 mm in length. The wall thickness thereof was 300 mm. The inside of the furnace was divided in series into four thermal decomposition chambers (N$_2$O decomposition zones), having a space of almost the same volume, with porous plates made of heat resistant bricks (thickness: 200 mm). The gas to be treated, which had been divided and preheated was fed into the first reaction chamber, while the remainder of the divided gas to be treated was introduced into the second, third and fourth reaction chambers. The second, third and fourth reaction chambers were each provided with inlets of the gas to be treated immediately after the hot gas stream was fed thereinto. These inlets of the gas to be treated were formed at two positions in opposition to each other on planes vertical to the major axis of the thermal decomposition reaction furnace in such a manner that the blow direction of the gas to be treated and the major axis did not intersect each other. A preheating portion, which was made of heat resistant bricks similar to the thermal decomposition portion, had a cylindrical shape with a space of 200 mm in inner diameter and 500 mm in length. It was provided with an inlet of the gas to be treated at one end while the other end was connected to the thermal decomposition portion. Into this preheating portion, methanol corresponding to 13 kcal per 1 Nm$^3$ of the gas to be treated was introduced with air at a rate of 0.0231 kmol/hr. Then it was subjected to combustion in the preheating portion and uniformly mixed with the gas to be treated introduced into the preheating portion at 17.8 Nm$^3$/hr. The temperature of the gas to be treated was adjusted to 550° C. The temperature of the gas stream introduced from the preheating portion to the first reaction chamber was 830° C. The gas to be treated at 550° C. was supplied into the second, third and fourth reaction chambers respectively at flow rates of 34.3 Nm$^3$/hr, 72.7 Nm$^3$/hr and 155.2 Nm$^3$/hr. The mixtures of the hot gas stream with the gas to be treated at the inlets of the second, third and fourth reaction chambers had each a temperature of 830° C. The pressure within the furnace was 1.25 kg/cm$^2$ (gauge pressure).

The temperature of the gas stream discharged from the thermal decomposition reaction furnace was 1162° C. and $N_2O$ contained in the supplied gas to be treated had been thus thermally decomposed at a ratio of 99% or more.

Example 8

The inside of the thermal decomposition reaction furnace as in Example 7 was divided in series into first, second and third chambers, having a space of almost the same volume, with porous plates made of heat resistant bricks (thickness: 200 mm). The inlets of the gas to be treated were arranged as in Example 7. The preheating portion had the same volume as in Example 7. $N_2O$ in the gas to be treated was thermally decomposed as in Example 7 but the flow rate of methanol supplied into the preheating portion being 0.0520 kmol/hr; and the flow rates of the gas to be treated supplied into the preheating portion and the second and third chambers being respectively 39.9 $Nm^3$/hr, 77.0 $Nm^3$/hr and 163.1 $Nm^3$/hr.

The pressure within the furnace was 1.25 kg/cm².

The temperatures of the gas stream mixtures in the preheating portion and at the inlets of the second and third chambers were each 830° C. The temperature of the gas stream discharged from the thermal decomposition reaction furnace was 1172° C. and $N_2O$ contained in the supplied gas to be treated had been thus thermally decomposed at a ratio of 99% or more.

Table 2 summarizes the conditions of the thermal decomposition of $N_2O$ and the results in the above Examples 1 to 8.

Comparative Example 1

The thermal decomposition reaction furnace as in Example 1 was provided with neither porous plate made of heat resistant bricks nor baffle plate. That is, the inside of the furnace was made a single reaction chamber and the $N_2O$-containing gas to be treated was supplied as a whole (i.e., not divided) exclusively into the preheating portion. Then $N_2O$ contained in the gas to be treated was thermally decomposed as in Example 1 but the flow rates of hydrogen and the gas to be treated supplied into the preheating portion being respectively 19.9 $Nm^3$/hr and 280 $Nm^3$/hr.

The pressure within the furnace was 1.25 kg/cm². The temperature of the gas stream mixture at the inlet of the thermal decomposition portion was 830° C. The temperature of the gas stream discharged from the thermal decomposition reaction furnace was 1283° C. and $N_2O$ contained in the supplied gas to be treated had been thermally decomposed at a ratio of 99% or more.

As described above, the temperature of the gas stream at the outlet of the thermal decomposition furnace was 1283° C. in Comparative Example 1, while the corresponding temperature in the above Example 2 was 1027° C., i.e., much lower (by 256° C.). In Comparative Example 1, 19.9 $Nm^3$/hr of hydrogen was employed to thermally decompose 280 $Nm^3$/hr of the gas to be treated. In, for example, Example 3 according to the invention, in contrast thereto, only 0.1 $Nm^3$/hr of hydrogen was supplied to thermally decompose the same amount (i.e., 280 $Nm^3$/hr) of the gas to be treated as in Comparative Example 1. $N_2O$ in the gas to be treated was thermally decomposed at a ratio of 99% or more in both of these Examples, which indicates that, in the invention, the heat generated in association with the decomposition of $N_2O$ in the thermal decomposition furnace can be very efficiently utilized by supplying the gas to be treated in portions.

Since the gas to be treated is preheated in the invention, only a small amount of a fuel is needed, as described above. In case where NO formed by the thermal decomposition of $N_2O$ is recovered if necessary, the NO product is diluted with the gas generated only at an extremely low dilution ratio and thus NO can be recovered at a high concentration.

Comparative Example 2

$N_2O$ in a gas to be treated was thermally decomposed without dividing the gas to be treated as in Comparative Example 1 but the flow rate of hydrogen supplied into the preheating portion being 2.9 $Nm^3$/hr.

The pressure within the furnace was 1.25 kg/cm². The temperatures of the gas stream mixture at the inlet of the thermal decomposition portion was 598° C. The temperature of the gas stream discharged from the thermal decomposition furnace was 601° C. and $N_2O$ contained in the supplied gas to be treated had not been thermally decomposed.

As described above, hydrogen was supplied at a flow rate of 2.9 $Nm^3$/hr in Comparative Example 2. However, $N_2O$ in 280 $Nm^3$/hr of the gas to be treated could not be thermally decomposed by using hydrogen in such a small amount. In, for example, Example 1 of the invention as described above, $N_2O$ in 280 $Nm^3$/hr of the gas to be treated could be thermally decomposed at a ratio of 99% or more by using only 1.3 $Nm^3$/hr of hydrogen.

Table 3 summarizes the conditions of the thermal decomposition of $N_2O$ and the results in the above Comparative Examples 1 and 2.

Example 9

$N_2O$ contained in a gas to be treated at 200° C., which had a composition of $N_2O$ (15.0% by mol), $O_2$ (13.5% by mol), $N_2$ (70.2% by mol), $CO_2$ (1.1% by mol), NO (0.1% by mol) and $NO_2$ (0.1% by mol) and was supplied at a flow rate of 130.6 $m^3$/H, was catalytically decomposed by using a catalyst.

The catalyst employed was a copper oxide/alumina catalyst. That is, use was made of a catalyst carrying 3.7% of copper oxide and having a surface area of 145 $m^2$/g and a packing density of 758 kg/$m^3$ prepared by impregnating γ-alumina with a copper nitrate solution, drying under a hot air stream at 120° C. for 6 hours and then baking at 500° C. for 3 hours.

The catalytic decomposition reactor employed was a cylindrical container of 2700 mm in inner diameter and 5000 mm in length. The inside of the reactor was divided into five catalytic decomposition reaction chambers ($N_2O$ decomposition zones) in opposition to the flow direction of the hot gas stream (i.e., in opposition to the longitudinal direction of the reactor). Mixing chambers partitioned with porous plates were located in front and at the back of each reaction chamber. The first, second, third, fourth and fifth reaction chambers had respectively 0.25 $m^3$, 0.14 $m^3$, 0.63 $m^3$, 2.27 $m^3$ and 6.61 $m^3$ of the catalyst.

130.6 $Nm^3$/H of the gas to be treated was divided into five gas streams. The preheated gas to be treated was fed into the first reaction chamber and formed a hot gas stream at the outlet of the first reaction chamber. Into the mixing chambers in front of the second, third, fourth and fifth reaction chambers, the remainder of the divided gas to be treated was respectively introduced each from two directions perpendicular to the hot gas stream flow direction in such a manner as to form a rotary stream.

The pressure at the inlet of the reactor was adjusted to 0.21 MPa. 12.5 $Nm^3$/H of the gas to be treated was heated to 430° C. by indirect heat-exchange with the outlet gas of the reactor and then supplied into the first reaction chamber. The gas at the outlet of the first reaction chamber was a hot gas at 779° C. due to the $N_2O$ decomposition heat. The gas to be treated was supplied at a rate of 10.0 $Nm^3/H$ to the mixing chamber in front of the second reaction chamber in such a manner as to give an $N_2O$ concentration of 6.5% by mol after mixing with the above-described hot gas. After mixing, the temperature of the gas attained 528° C. The gas at the outlet of the second reaction chamber was a hot gas at 685° C. due to the $N_2O$ decomposition heat. The gas to be treated was supplied at a rate of 18.1 $Nm^3/H$ to the mixing chamber in front of the third reaction chamber. After mixing, the gas showed an $N_2O$ concentration of 6.5% by mol and a temperature of 473° C. The gas at the outlet of the third reaction chamber was a hot gas at 632° C. due to the $N_2O$ decomposition heat. The gas to be treated was supplied at a rate of 32.6 $Nm^3/H$ to the mixing chamber in front of the fourth reaction chamber. After mixing, the gas showed an $N_2O$ concentration of 6.5% by mol and a temperature of 443° C. The gas at the outlet of the fourth reaction chamber was a hot gas at 603° C. due to the $N_2O$ decomposition heat. The gas to be treated was supplied at a rate of 57.4 $Nm^3/H$ to the mixing chamber in front of the fifth reaction chamber. After mixing, the gas showed an $N_2O$ concentration of 6.5% by mol and a temperature of 426° C. The temperature of the decomposed gas at the outlet of the fifth reaction chamber was 587° C. Thus, $N_2O$ contained in the supplied gas to be treated had been catalytically decomposed at a ratio of 99% or more.

The total amount of the gas to be treated in this Example amounts to 130.6 $m^3/H$. Since the gas to be treated is supplied in portions, a 12.5 $m^3/H$ portion alone in 130.6 $m^3/H$ is preheated to the initiation temperature of the reaction of 430° C. before supplying. Thus, the heat load on the heat exchanger required for preheating is 908 kcal/h. The remainder of the divided gas to be treated can be supplied without preheating. Although the remainder of the gas to be treated is supplied without preheating, the inlet temperature of each catalytic bed can be maintained at 430° C. (i.e., the initiation temperature of the reaction) or higher and $N_2O$ can be catalytically decomposed continuously, as this Example clearly shows.

Example 10

$N_2O$ contained in a gas to be treated discharged from an adipic acid plant having the composition and flow rate as given in Table 4 was catalytically decomposed by using a catalyst. The same catalyst as that of Example 9 was employed.

The catalytic decomposition reactor employed was a cylindrical container of 2700 mm in inner diameter and 5000 mm in length. The inside of the reactor was divided into two catalytic decomposition reaction chambers in opposition to the flow direction of the hot gas stream. A mixing chamber partitioned with porous plates was located between these reaction chambers. The first and second reaction chambers had respectively 3.90 $m^3$ and 6.04 $m^3$ of the catalyst.

The preheated gas to be treated was fed into the first reaction chamber, together with a diluent gas while the remainder of the divided gas to be treated was introduced into the mixing chamber in front of the second reaction chamber from two positions perpendicular to the hot gas stream flow direction in such a manner as to form a rotary stream.

The pressure at the inlet of the reactor was adjusted to 0.21 MPa. 114.8 $Nm^3/H$ of the gas to be treated at 30° C. and 406.7 $Nm^3/H$ of a diluent gas at 230° C. were mixed together in the first reaction chamber to thereby give an $N_2O$ concentration of 7.5% by mol. Further, the gas mixture was subjected to indirect heat-exchange with the outlet gas of the reactor to attain a temperature of 500° C.

The above-described diluent gas was one obtained by heat-recovery with the use of a boiler from the reaction mixture after catalytically decomposing $N_2O$ in the gas to be treated.

The gas stream at the outlet of the first reaction chamber was a hot gas at 680° C. heated by the $N_2O$ decomposition heat.

165.2 $Nm^3/H$ of the gas to be treated and 44.1 $Nm^3/H$ of the diluent gas were mixed together in the mixing chamber in front of the second reaction chamber to thereby give an $N_2O$ concentration of 7.5% by mol and a gas temperature of 500° C. The temperature of the decomposed gas at the outlet was 680° C. Thus, $N_2O$ contained in the supplied gas to be treated had been catalytically decomposed at a ratio of 99% or more. The ratio of the total amount of the diluent gas employed to the supplied gas to be treated was 1.61.

Example 11

The same catalyst as employed in Example 9 was used. The catalytic decomposition reactor employed was a cylindrical container of 2700 mm in inner diameter and 5000 mm in length. The inside of the reactor was divided into three catalytic decomposition reaction chambers in opposition to the flow direction of the hot gas stream. Mixing chamber partitioned with porous plates were located in front of each reaction chamber. The first, second and third reaction chambers had respectively 2.07 $m^3$, 3.08 $m^3$ and 4.70 $m^3$ of the catalyst.

The preheated gas mixture of the gas to be treated with the diluent gas was fed into the first reaction chamber, while the remainder of the divided gas to be treated and the diluent gas were introduced into the mixing chambers in front of the second and third reaction chambers each from two positions perpendicular to the hot gas stream flow direction (i.e., the longitudinal direction of the reactor) in such a manner as to form a rotary stream.

The pressure at the inlet of the reactor was adjusted to 0.21 MPa. 62.0 $Nm^3/H$ of the gas to be treated at 30° C. and 219.2 $Nm^3/H$ of a diluent gas at 230° C. were mixed together in the first reaction chamber to thereby give an $N_2O$ concentration of 7.5% by mol. Further, the gas mixture was subjected to indirect heat-exchange with the outlet gas of the reactor to attain a temperature of 500° C.

The above-described diluent gas was one obtained by heat-recovery with the use of a boiler from the reaction mixture after catalytically decomposing $N_2O$ in the gas to be treated.

The gas stream at the outlet of the first reaction chamber was a hot gas at 680° C. heated by the $N_2O$ decomposition heat. 89.3 $Nm^3/H$ of the gas to be treated and 23.8 $Nm^3/H$ of a diluent gas were supplied into the mixing chamber in front of the second reaction chamber. After mixing, the gas showed an $N_2O$ concentration of 7.5% by mol and a temperature of 500° C. The gas stream at the outlet of the second reaction chamber was a hot gas at 680° C. heated by the $N_2O$ decomposition heat. 128.7 $Nm^3/H$ of the gas to be treated and 34.2 $Nm^3/H$ of a diluent gas were supplied into the mixing chamber in front of the third reaction chamber. After mixing, the gas showed an $N_2O$ concentration of 7.5% by mol and a temperature of 500° C. The gas stream at the outlet was a hot gas at 680° C. Thus, $N_2O$ contained in the supplied gas to be treated had been catalytically decomposed at a ratio of 99% or more. The ratio of the total amount of the diluent gas employed to the supplied gas to be treated was 0.99.

Example 12

The same catalyst as employed in Example 9 was used. The catalytic decomposition reactor employed was a cylindrical container having an inner diameter of 2700 mm and a length of 5000 mm. The inside of the reactor was divided into four catalytic decomposition reaction chambers in opposition to the flow direction of the hot gas stream. Mixing chamber partitioned with porous plates were located in front of each reaction chamber. The first, second, third and fourth reaction chambers had respectively 1.24 m$^3$, 1.81 m$^3$, 2.69 m$^3$ and 4.07 m$^3$ of the catalyst.

The preheated gas mixture of the gas to be treated with the diluent gas was fed into the first reaction chamber, while the remainder of the divided gas to be treated and the diluent gas were introduced into the mixing chambers in front of the second, third and fourth reaction chambers each from two positions perpendicular to the hot gas stream flow direction (i.e., the longitudinal direction of the reactor) in such a manner as to form a rotary stream.

The pressure at the inlet of the reactor was adjusted to 0.21 MPa. 37.4 Nm$^3$/H of the gas to be treated at 30° C. and 131.6 Nm$^3$/H of a diluent gas at 230° C. were mixed together in the first reaction chamber to thereby give an N$_2$O concentration of 7.5% by mol. Further, the gas mixture was subjected to indirect heat-exchange with the outlet gas of the reactor to attain a temperature of 500° C.

The above-described diluent gas was one obtained by heat-recovery with the use of a boiler from the reaction mixture after catalytically decomposing N$_2$O in the gas to be treated.

The gas stream at the outlet of the first reaction chamber was a hot gas at 680° C. heated by the N$_2$O decomposition heat. 53.8 Nm$^3$/H of the gas to be treated and 14.3 Nm$^3$/H of a diluent gas were supplied into the mixing chamber in front of the second reaction chamber. After mixing, the gas showed an N$_2$O concentration of 7.5% by mol and a temperature of 500° C. The gas stream at the outlet of the second reaction chamber was a hot gas at 680° C. heated by the N$_2$O decomposition heat. 77.4 Nm$^3$/H of the gas to be treated and 20.5 Nm$^3$/H of a diluent gas were supplied into the mixing chamber in front of the third reaction chamber. After mixing, the gas showed an N$_2$O concentration of 7.5% by mol and a temperature of 500° C. The gas stream at the outlet of the third reaction chamber was a hot gas at 680° C. heated by the N$_2$O decomposition heat. 111.4 Nm$^3$/H of the gas to be treated and 29.6 Nm$^3$/H of a diluent gas were supplied into the mixing chamber in front of the fourth reaction chamber. After mixing, the gas showed an N$_2$O concentration of 7.5% by mol and a temperature of 500° C. The gas stream at the outlet was a hot gas at 680° C. Thus, N$_2$O contained in the supplied gas to be treated had been catalytically decomposed at a ratio of 99% or more. The ratio of the total amount of the diluent gas employed to the supplied gas to be treated was 0.70.

Example 13

The same catalyst as employed In Example 9 was used. The catalytic decomposition reactor employed was a cylindrical container of 2700 mm in inner diameter and 5000 mm in length. The inside of the reactor was divided into five catalytic decomposition reaction chambers in opposition to the flow direction of the hot gas stream. Mixing chamber partitioned with porous plates were located in front of each reaction chamber. The first, second, third, fourth and fifth reaction chambers had respectively 0.78 m$^3$, 1.14 m$^3$, 1.67 m$^3$, 2.48 m$^3$ and 3.73 m$^3$ of the catalyst.

The preheated gas mixture of the gas to be treated with the diluent gas was fed into the first reaction chamber, while the remainder of the divided gas to be treated and the diluent gas were introduced into the mixing chambers in front of the second, third, fourth and fifth reaction chambers each from two positions perpendicular to the hot gas stream flow direction (i.e., the longitudinal direction of the reactor) in such a manner as to form a rotary stream.

The pressure at the inlet of the reactor was adjusted to 0.21 MPa. 23.7 Nm$^3$/H of the gas to be treated at 30° C. and 83.8 Nm$^3$/H of a diluent gas at 230° C. were mixed together in the first reaction chamber to thereby give an N$_2$O concentration of 7.5% by mol. Further, the gas mixture was subjected to indirect heat-exchange with the outlet gas of the reactor to attain a temperature of 500° C.

The above-described diluent gas was one obtained by heat-recovery with the use of a boiler from the reaction mixture after catalytically decomposing N$_2$O in the gas to be treated.

The gas stream at the outlet of the first reaction chamber was a hot gas at 680° C. heated by the N$_2$O decomposition heat. 34.2 Nm$^3$/H of the gas to be treated and 9.1 Nm$^3$/H of a diluent gas were supplied into the mixing chamber in front of the second reaction chamber. After mixing, the gas showed an N$_2$O concentration of 7.5% by mol and a temperature of 500° C. The gas stream at the outlet of the second reaction chamber was a hot gas at 680° C. heated by the N$_2$O decomposition heat. 49.2 Nm$^3$/H of the gas to be treated and 13.1 Nm$^3$/H of a diluent gas were supplied into the mixing chamber in front of the third reaction chamber. After mixing, the gas showed an N$_2$O concentration of 7.5% by mol and a temperature of 500° C. The gas stream at the outlet of the third reaction chamber was a hot gas at 680° C. heated by the N$_2$O decomposition heat. 70.9 Nm$^3$/H of the gas to be treated and 18.9 Nm$^3$/H of a diluent gas were supplied into the mixing chamber in front of the fourth reaction chamber. After mixing, the gas showed an N$_2$O concentration of 7.5% by mol and a temperature of 500° C. The gas stream at the outlet of the fourth reaction chamber was a hot gas at 680° C. heated by the N$_2$O decomposition heat. 102.0 Nm$^3$/H of the gas to be treated and 27.2 Nm$^3$/H of a diluent gas were supplied into the mixing chamber in front of the fifth reaction chamber. After mixing, the gas showed an N$_2$O concentration of 7.5% by mol and a temperature of 500° C. The gas stream at the outlet was a hot gas at 680° C. Thus, N$_2$O contained in the supplied gas to be treated had been catalytically decomposed at a ratio of 99% or more. The ratio of the total amount of the diluent gas employed to the supplied gas to be treated was 0.54.

Table 5 summarizes the conditions of the catalytic decomposition of N$_2$O and the results in the above Examples 10 to 13.

Comparative Example 3

The same catalyst and gas to be treated as employed in Example 9 were used. The catalytic decomposition reactor employed was a cylindrical container of 2700 mm in inner diameter and 5000 mm in length composed of a single reaction chamber. The reaction chamber had 2.60 m$^3$ of the catalyst.

The preheated gas to be treated was fed into the reaction chamber. The pressure at the inlet of the reactor was adjusted to 0.21 MPa. 130.6 Nm³/H of the gas to be treated was subjected to indirect heat-exchange with the outlet gas of the reactor to attain a temperature of 430° C. and then supplied into the reaction chamber. The gas stream at the outlet of the reaction chamber was a hot gas at 779° C. heated by the $N_2O$ decomposition heat. Thus, $N_2O$ contained in the supplied gas to be treated had been catalytically decomposed at a ratio of 99% or more. In this Comparative Example 3, the heat load required in preheating was 9,623 kcal/h. Accordingly, use should be made in this case of a large-scaled heat exchanger with which 11 times as much heat can be subjected to heat-exchange as compared to the case of Example 9.

Comparative Example 4

The same catalyst and gas to be treated as employed in Example 10 were used. The catalytic decomposition reactor employed was a cylindrical container of 2700 mm in inner diameter and 5000 mm in length composed of a single reaction chamber. The reaction chamber had 10.18 m³ of the catalyst.

The preheated mixture of the gas to be treated and the diluent gas was fed into the reaction chamber. The pressure at the inlet of the reactor was adjusted to 0.21 MPa. 280.0 Nm³/H of the gas to be treated at 30° C. and 989.8 Nm³/H of the gas to be treated at 230° C. were mixed together to give an $N_2O$ concentration of 7.5% by mol. Further, the gas mixture was subjected to indirect heat-exchange with the outlet gas of the reactor to attain a temperature of 500° C. followed by supplying.

The above-described diluent gas was one obtained by heat-recovery with the use of a boiler from the reaction mixture after catalytically decomposing $N_2O$ in the gas to be treated.

The gas stream at the outlet of the reaction chamber was a hot gas at 680° C. heated by the $N_2O$ decomposition heat. Thus, $N_2O$ contained in the supplied gas to be treated had been catalytically decomposed at a ratio of 99% or more. The ratio of the total amount of the diluent gas employed to the supplied gas to be treated was 3.54.

As described above, 3.54 times as much diluent gas was required in catalytically decomposing 280.0 Nm³/H of the gas to be treated by using a catalyst in Comparative Example 4. In contrast thereto, only 0.54 times as much diluent gas was required in Example 13 according to the invention. In Comparative Example 4, furthermore, the sum of the diluent gas and the gas to be treated to be heated at the inlet of the first stage amounted to 1269.8 Nm³/H, while the corresponding amount of the gases in Example 12 was as small as 432.1 Nm³/H. Since $N_2O$ in the gas to be treated could be decomposed at a ratio of 99% or more in each case, it is obvious that, in the invention, the heat generated in association of the decomposition of $N_2O$ in the catalytic decomposition reactor can be more efficiently utilized by supplying the gas to be treated in portions.

Table 6 summarizes the conditions of the catalytic decomposition of $N_2O$ and the results in the above Comparative Example 4.

TABLE 1

| | Composition of $N_2O$-containing gas (gas to be treated) | |
|---|---|---|
| | Discharged gas composition (mol %) | Discharged gas flow rate (Nm³/H) |
| $N_2O$ | 33.9 | 94.9 |
| NO | 0.3 | 0.8 |
| $NO_2$ | 0.4 | 1.1 |
| $CO_2$ | 2.4 | 6.7 |
| $O_2$ | 4.2 | 11.8 |
| $N_2$ | 58.9 | 164.9 |
| Total | 100.0 | 280.2 |

TABLE 2

| | Reaction conditions and results | | | | | | | |
|---|---|---|---|---|---|---|---|---|
| | Ex. 1 | Ex. 2 | Ex. 3 | Ex. 4 | Ex. 5 | Ex. 6 | Ex. 7 | Ex. 8 |
| No. of stages supplying gas to be treated | 4 | 4 | 4 | 4 | 3 | 2 | 4 | 3 |
| Supplying temp. (° C.) | 550 | 300 | 700 | 550 | 550 | 550 | 550 | 550 |
| Amount of Hydrogen (Nm³/hr) | 1.3 | 7.2 | 0.1 | 1.2 | 2.9 | 6.9 | — | — |
| Amount of Methanol (kmol/hr) | — | — | — | — | — | — | 0.0231 | 0.0520 |
| $H_2$ or MeOH (kcal) (per 1 Nm³ of gas to be treated) | 12 | 66 | 0.9 | 11 | 26 | 63 | 13 | 28 |
| Pressure (kg/cm²) | 1.25 | 1.25 | 1.25 | 1.25 | 1.25 | 1.25 | 1.25 | 1.25 |
| Feed (Nm³/H) of gas to be treated | | | | | | | | |
| Preheating portion | 17.9 | 55.7 | 3 | 19.7 | 40.4 | 96.6 | 17.8 | 39.9 |
| Chamber 2 | 34.1 | 60.0 | 12.0 | 36.1 | 76.5 | 183.4 | 34.3 | 77.0 |
| Chamber 3 | 72.6 | 72.9 | 50.6 | 73.4 | 163.1 | — | 72.7 | 163.1 |
| Chamber 4 | 155.4 | 91.4 | 214.4 | 150.8 | — | — | 155.2 | — |
| Inlet temp. (° C.) | | | | | | | | |
| Chamber 1 | 830 | 830 | 830 | 800 | 830 | 830 | 830 | 830 |
| Chamber 2 | 830 | 830 | 830 | 800 | 830 | 830 | 830 | 830 |
| Chamber 3 | 830 | 830 | 830 | 800 | 830 | — | 830 | 830 |

TABLE 2-continued

Reaction conditions and results

|  | Ex. 1 | Ex. 2 | Ex. 3 | Ex. 4 | Ex. 5 | Ex. 6 | Ex. 7 | Ex. 8 |
|---|---|---|---|---|---|---|---|---|
| Chamber 4 | 830 | 830 | 830 | 800 | — | — | 830 | — |
| Final outlet temp. (° C.) | 1163 | 1027 | 1263 | 1131 | 1173 | 1200 | 1162 | 1172 |
| $N_2O$ decomposition ratio (%) | >99 | >99 | >99 | >99 | >99 | >99 | >99 | >99 |

Note:
1. Pressure is expressed in gauge pressure.
2. Preheating portion is referred to as the first stage.

TABLE 3

Reaction conditions and Results of Comparative Examples 1 and 2

|  | Compa. Ex. 1 | Compa. Ex. 2 |
|---|---|---|
| No. of stages supplying gas to be treated | 1 | 1 |
| supplying temp. (° C.) | 550 | 550 |
| Amount of Hydrogen (Nm³/hr) | 19.9 | 2.9 |
| " (kcal/ Nm³) - treated gas | 182 |  |
| Reaction pressure (kg/cm²) | 1.25 | 1.25 |
| Feed (Nm³/H) of gas to be treated | 280 | 280 |
| Initiation temp. (° C.) | 830 | 598 |
| Final outlet temp. (° C.) | 1283 | 601 |
| Reaction ratio (%) | 99 | 0 |

Pressure is expressed in gauge pressure.

TABLE 4

Composition and flow rate of $N_2O$-containing gas to be treated)

|  | Discharged gas composition (mol %) | Discharged gas flow rate (Nm³/H) |
|---|---|---|
| $N_2O$ | 34.1 | 95.5 |
| NO | 0.1 | 0.3 |
| $NO_2$ | 0.1 | 0.3 |
| $CO_2$ | 2.4 | 6.7 |
| $O_2$ | 4.0 | 11.2 |
| $N_2$ | 59.3 | 166.0 |
| Total | 100.0 | 280.0 |

TABLE 5

Reaction conditions and results

|  | Ex. 10 | Ex. 11 | Ex. 12 | Ex. 13 |
|---|---|---|---|---|
| No. of stages supplying gas to be treated | 2 | 3 | 4 | 5 |
| Supplying temp. (° C.) | 30 | 30 | 30 | 30 |
| Diluent gas temp. (° C.) | 230 | 230 | 230 | 230 |
| Inlet temp. at each stage (° C.) | 500 | 500 | 500 | 500 |
| Outlet temp. at each stage (° C.) | 680 | 680 | 680 | 680 |
| Pressure at reactor inlet (MPa) | 0.21 | 0.21 | 0.21 | 0.21 |
| Feed of gas to be treated (Nm³/H) | 114.8 | 62.0 | 37.4 | 23.7 |
| Stage 1 | 165.2 | 89.3 | 53.8 | 34.2 |
| Stage 2 | — | 128.7 | 77.4 | 49.2 |
| Stage 3 | — | — | 111.4 | 70.9 |
| Stage 4 | — | — | — | 102.0 |
| Stage 5 | 280.0 | 280.0 | 280.0 | 280.0 |
| Σ |  |  |  |  |
| Feed of diluent gas (Nm³/H) | 406.7 | 219.2 | 131.6 | 83.8 |
| Stage 1 | 44.1 | 23.8 | 14.3 | 9.1 |
| Stage 2 | — | 34.2 | 20.5 | 13.1 |
| Stage 3 | — | — | 29.6 | 18.9 |
| Stage 4 | — | — | — | 27.2 |
| Stage 5 | 450.8 | 277.2 | 196.0 | 152.1 |
| Σ |  |  |  |  |
| Σ Diluent gas/Σ gas to be treated (molar ratio) | 1.61 | 0.99 | 0.70 | 0.54 |
| Catalytic bed volume (m³) | 3.90 | 2.07 | 1.24 | 0.78 |
| Stage 1 | 6.04 | 3.08 | 1.81 | 1.14 |
| Stage 2 | — | 4.70 | 2.69 | 1.67 |
| Stage 3 | — | — | 4.07 | 2.48 |
| Stage 4 | — | — | — | 3.73 |
| Stage 5 | 9.93 | 9.85 | 9.82 | 9.80 |
| Σ |  |  |  |  |
| $N_2O$ conversion (%) | >99 | >99 | >99 | >99 |

TABLE 6

Reaction conditions and results of Comparative Example 4

|  | Compara. Example 4 |
|---|---|
| Discharged gas: Feed Stage number | 1 |
| Discharged gas: Feed temp. (° C.) | 30 |
| Diluent gas temp. (° C.) | 230 |
| Inlet temp. (° C.) | 500 |
| Outlet temp. (° C.) | 680 |
| Reactor inlet pressure (MPa) | 0.21 |
| Diluent gas flow rate (Nm³/H) | 989.8 |
| Σ Diluent gas/Σ gas to be treated (molar ratio) | 3.54 |
| Catalytic bed volume (m³) | 10.18 |
| $N_2O$ conversion (%) | >99 |

INDUSTRIAL APPLICABILITY

As the detailed description given above clearly indicates, the present invention provides a highly useful method in practice for preventing global warming which makes it possible to efficiently decompose $N_2O$ at a low temperature while externally supplying only an extremely small amount of energy, and an apparatus therefor. The invention achieves remarkable effects as will be shown hereinafter.

That is to say, the invention for preventing global warming by thermally decomposing $N_2O$ achieves the following effects.

1. It exerts remarkably excellent effects such that $N_2O$ can be thermally decomposed at a high decomposition ratio at a relatively low temperature; that the thus formed NO and $NO_2$ exist at high concentrations and can be economically recovered, if needed; and that only a very small amount of heat energy is supplied externally.

2. The invention can provide an apparatus which is highly useful in practice and has the merits such as having a small reactor volume; the materials of the process instruments thereof being easily selected; only a small heat load being applied on the process instruments thereof; a smaller heat exchanger being usable in heating the gas to be treated; and making it possible to recover NO, etc. at high concentration.

On the other hand, the invention for preventing global warming by catalytically decomposing $N_2O$ achieves the following effects.

1. In the method of decomposing $N_2O$ according to the invention, the $N_2O$-containing gas to be treated is divided and a portion thereof is preheated to the temperature at which the catalytic decomposition of $N_2O$ can be initiated while the remainder of the divided gas to be treated is supplied into an $N_2O$ catalytic decomposition bed at a temperature lower than the temperature of the preheated gas as described above. Thus, the amount of the heat required in preheating can be considerably reduced, compared with the case wherein the whole gas to be treated is preheated and then supplied.

2. Therefore, the preheating devices (for example, a heat exchanger) to be used can be considerably reduced in size. When the preheating is carried out by combustion of a fuel supplied externally, the amount of the fuel can be significantly reduced.

3. In the invention, it is also possible that the gas to be treated is mixed with a diluent gas and supplied into the catalytic bed. In this case, the amount of the diluent gas to be used can be largely reduced owing to the effects achieved by supplying the gas to be treated in portions as described above.

4. According to the method of the invention, $N_2O$ is catalytically decomposed by using a catalytic bed. Thus, the heat formed in a large amount in association with the catalytic decomposition of $N_2O$ in the former catalytic bed can be successively given to the catalytic bed located posterior in the longitudinal direction. That is, the heat formed in a large amount by the catalytic decomposition of $N_2O$ can be very efficiently utilized in elevating the temperature of the gas stream to be treated successively supplied in portions.

5. Thus, the temperature of the gas to be supplied into each catalytic bed and the temperature in each catalytic bed can be easily controlled at an appropriate level for the desired catalytic system.

6. The apparatus of catalytic decomposition of $N_2O$ according to the invention makes it possible to embody the above-described method for catalytically decomposing $N_2O$ to give the effects as described above. Since the whole apparatus can be molded in a smaller size, various costs thereof can be reduced. Moreover, the amount of a fuel or energy supplied externally can be considerably reduced.

7. By using this apparatus, the temperature of the catalytic decomposition bed can be very easily controlled and a rapid increase in temperature at the catalytic bed or around the same due to the decomposition heat of $N_2O$ can be prevented without fail.

8. Thus, the $N_2O$ catalytic decomposition apparatus of the invention can be operated easily and, moreover, has an excellent durability, thereby being highly useful in practice.

9. In the process for producing adipic acid according to the present invention, $N_2O$ is released into the atmosphere only in a very small amount. Since this process depends on the $N_2O$-decomposition, techniques being highly useful in practice as described above, it largely contributes to the prevention of global warming. In addition, it can be economically carried out at a low equipment cost.

What is claimed is:

1. A method for thermally or catalytically decomposing $N_2O$, which is a global warming agent, in a $N_2O$-containing gas to be treated, said method comprising dividing the $N_2O$-containing gas stream to be treated in portions, preheating a portion thereof so as to exothermally decompose $N_2O$ in said gas stream to form a hot gas stream, and supplying the remainder of the divided gas stream to be treated into said hot gas stream to thereby continuously decompose $N_2O$.

2. The method as claimed in claim 1, wherein said exothermic decomposition of $N_2O$ is performed by thermal decomposition without using any catalyst.

3. The method as claimed in claim 2, wherein the remainder of said divided gas to be treated is supplied into plural positions in the flow direction of said hot gas stream.

4. The method as claimed in claim 3, wherein said decomposition of $N_2O$ in the gas to be treated is performed in a state of a substantially plug flow.

5. The method as claimed in claim 3, wherein said preheating is performed by a direct heating system utilizing an oxidative exothermic reaction of a fuel.

6. The method as claimed in claim 5, wherein said fuel is hydrogen or methanol.

7. The method as claimed in claim 1, wherein said exothermic decomposition of $N_2O$ is performed by catalytic decomposition.

8. The method as claimed in claim 7, wherein the remainder of said divided gas to be treated is supplied into plural positions in the flow direction of said hot gas stream and each is brought into contact with a catalytic bed respectively.

9. The method as claimed in claim 8, wherein the gas stream, immediately before contacting the catalytic bed, is a mixture with a diluent gas.

10. The method as claimed in claim 9, wherein said diluent gas is air and/or the gas, which has been subjected to the catalytic decomposition of $N_2O$ in the gas to be treated.

11. The method as claimed in claim 10, wherein said preheating is performed by mixing the gas to be treated and/or the diluent gas with steam formed by reacting hydrogen and oxygen using a noble metal catalyst.

12. The method as claimed in claim 9, wherein the gas having been subjected to the catalytic decomposition of $N_2O$ in the gas to be treated is cooled and then used as the diluent gas.

13. The method as claimed in claim 12, wherein said preheating is performed by mixing the gas to be treated and/or the diluent gas with steam formed by reacting hydrogen and oxygen using a noble metal catalyst.

14. The method as claimed in claim 1, wherein said $N_2O$ is decomposed to a gas comprising $N_2$ and little, if any, NO and $NO_2$.

15. The method as claimed in claim 1, wherein said $N_2O$ is decomposed toga gas consisting essentially of $N_2$.

16. An apparatus for thermally decomposing $N_2O$, which is a global warming agent, in a $N_2O$-containing gas, said apparatus comprising:

(a) an introduction portion for the $N_2O$-containing gas to be treated;

(b) a preheating portion for the thus introduced gas to be treated;

(c) a thermal decomposition portion adjacent to the preheating portion, said thermal decomposition portion having a component for supplying the gas to be treated and having a porous plate and/or a multi-pipe nozzle, said supplying component being provided at one or more positions in the flow direction of a gas stream; and (d) a discharging portion for the thermally decomposed gas.

17. The apparatus as claimed in claim 16, wherein said preheating portion has a fuel combustion component.

18. The apparatus as claimed in claim 17, wherein the temperature of the gas stream at the outlet of said discharging portion is controlled to a constant level by controlling the amount of the fuel fed into said fuel-combustion component.

19. The apparatus as claimed in claim 17, wherein said porous plate, multi-pipe nozzle and/or inlet of the gas to be treated are located in such a manner that the gas stream flowing towards the component for supplying the gas to be treated flows as a rotary stream.

20. An apparatus for catalytic decomposition of $N_2O$, which is a global warming agent, in a $N_2O$-containing gas, said apparatus comprising:

a device which comprises:
(a) an introduction portion for the gas to be treated and/or a diluent gas;
(b) a mixing portion for the gas to be treated and/or the diluent gas;
(c) a catalytic decomposition portion having a catalytic bed; and
(d) a discharging portion for the catalytically decomposed gas; and one or more devices each of which comprises:
(e) an introduction portion for the discharged gas having been catalytically decomposed, the gas to be treated and/or a diluent gas;
(f) a mixing portion for the discharged gas having been catalytically decomposed, the gas to be treated and/or the diluent gas;
(g) a catalytic decomposition portion having a catalytic bed; and
(h) a discharging portion for the catalytically decomposed gas.

21. The apparatus as claimed in claim 20, wherein said mixing portion for the gas to be treated and/or the diluent gas involves a preheating portion for the gas to be treated and/or the diluent gas.

22. A process for producing adipic acid with reduced release of $N_2O$ that causes global warming, comprising:

(1) a nitric acid-oxidation step in which cyclohexanol and/or cyclohexanone are oxidized with nitric acid to form adipic acid;

(2) a nitric acid recovery step in which $HNO_3$ is recovered from a $N_2O$-containing gas caused in the nitric acid-oxidation step;

(3) a $N_2O$ decomposition step in which the remaining $N_2O$-containing gas stream to be treated, from which $HNO_3$ has been recovered, is divided, a portion thereof is preheated to exothermally decompose $N_2O$ in the gas stream to form a hot gas stream, and the remainder of the divided gas stream to be treated is supplied into said hot gas stream to thereby continuously decompose $N_2O$; and (4) a $N_2O$ decomposition heat recovery step in which the $N_2O$ decomposition heat emitted from the $N_2O$ decomposition step is recovered.

23. The process as claimed in claim 22, wherein said $N_2O$ is decomposed in step (3) to a gas comprising $N_2$ and little, if any, NO and $NO_2$.

24. The process as claimed in claims 22, wherein said $N_2O$ is decomposed in step (3) to a gas consisting essentially of $N_2$.

25. An apparatus for thermally decomposing $N_2O$-containing gas, said apparatus comprising:

(a) an introduction section wherein the $N_2O$-containing gas is divided into at least two portions;
(b) a preheating section for at least one of the at least two portions of the $N_2O$-containing gas from the introduction section (a);
(c) a thermal decomposition section positioned adjacent to the preheating section, said thermal decomposition section having a component for supplying at least one of the at least two portions of the $N_2O$-containing gas from the introduction section (a) without entering preheating section (b), said supplying component being provided at one or more positions in the flow direction of a gas stream; and
(d) a discharging section for the thermally decomposed gas.

26. An apparatus for bringing $N_2O$, which is a global warming agent, in a $N_2O$-containing gas into contact with a catalytic bed to thereby catalytically decompose $N_2O$, said apparatus comprising:

(a) an introduction portion for the gas to be treated and/or a diluent gas;
(b) a mixing portion for the gas to be treated and/or the diluent gas;
(c) a mixing portion having one or more components for supplying the gas to be treated and/or the diluent gas at different positions in the longitudinal direction of the apparatus;
(d) a catalytic decomposition portion having the catalytic bed; and
(e) a discharging portion for the catalytically decomposed gas.

27. The apparatus as claimed in claim 26, wherein said mixing portion for the gas to be treated and/or the diluent gas involves a preheating portion for the gas to be treated and/or the diluent gas.

* * * * *